(12) United States Patent
McKeever

(10) Patent No.: US 7,185,288 B2
(45) Date of Patent: Feb. 27, 2007

(54) OPERATOR INTERFACE MODULE SEGMENTED BY FUNCTION IN AN AUTOMATIC CLINICAL ANALYZER

(75) Inventor: Robert Thomas McKeever, Landenberg, PA (US)

(73) Assignee: Dade Behring Inc., Deerfield, IL (US)

( * ) Notice: Subject to any disclaimer, the term of this patent is extended or adjusted under 35 U.S.C. 154(b) by 88 days.

(21) Appl. No.: 10/742,299

(22) Filed: Dec. 19, 2003

(65) Prior Publication Data
US 2005/0013736 A1    Jan. 20, 2005

Related U.S. Application Data

(60) Provisional application No. 60/488,689, filed on Jul. 18, 2003.

(51) Int. Cl.
*G06F 3/00* (2006.01)
*B32B 5/02* (2006.01)

(52) U.S. Cl. .................. 715/792; 715/771; 715/789; 715/793; 422/63

(58) Field of Classification Search ................ 715/771, 715/789, 792, 793
See application file for complete search history.

(56) References Cited

U.S. PATENT DOCUMENTS

| | | | |
|---|---|---|---|
| 4,678,755 A | 7/1987 | Shinohara et al. | |
| 5,254,311 A | 10/1993 | Ushikubo | |
| 5,316,726 A | 5/1994 | Babson et al. | |
| 5,719,059 A | 2/1998 | Mimura et al. | |
| 5,730,124 A | 3/1998 | Yamauchi | |
| 5,730,939 A | 3/1998 | Kurumada et al. | |
| 5,751,965 A * | 5/1998 | Mayo et al. ................ | 709/224 |
| 5,777,902 A | 7/1998 | Ono et al. | |
| 5,885,530 A | 3/1999 | Babson | |
| 5,896,086 A | 4/1999 | Ida | |
| 6,080,364 A | 6/2000 | Mimura et al. | |
| 6,090,630 A | 7/2000 | Koakutsu et al. | |
| 6,138,150 A * | 10/2000 | Nichols et al. ............ | 709/219 |
| 6,275,150 B1 | 8/2001 | Mandler et al. | |
| 6,426,761 B1 * | 7/2002 | Kanevsky et al. .......... | 715/788 |
| 6,544,476 B1 | 4/2003 | Mimura et al. | |
| 6,750,878 B1 * | 6/2004 | Tatsuo et al. ............... | 715/705 |
| 6,750,879 B2 * | 6/2004 | Sandberg .................... | 715/714 |
| 6,846,457 B1 * | 1/2005 | Tokiwa et al. ............... | 422/67 |

\* cited by examiner

*Primary Examiner*—Sy D. Luu
(74) *Attorney, Agent, or Firm*—Leland K. Jordan

(57) ABSTRACT

A method for displaying the status of a clinical analyzer on an operator interface in a manner that minimizes the effort required by the operator to access pertinent data. In one aspect the method includes displaying routine and non-routine information about the operational aspects of a clinical analyzer so that non-routine operational information screens is accessible only by qualified technicians.

9 Claims, 25 Drawing Sheets

Calibration Acceptance Criteria

| Method | GLU | Module ID | |
|---|---|---|---|
| Units | mg/dL | Flex Server | A |
| Calc Type | LINEAR | Flex Lot | 03002 |
| Date | 2003-6-23 02:43:22 | Cal. Catalog # | 01001 |
| Operator | MJB | Cal Lot | 323122 |
| Instrument S/N | 0662 | | |

Acceptance Criteria

| | Acceptance Criteria | Range | Value | Outcome |
|---|---|---|---|---|
| AC 1 | Average of recovered level 1 bottle values is within allowed recovered level 1 range. (accuracy) | xxxx | YYYY | |
| AC 2 | Recovered calibrator bottle values is within allowed recovered level % bias at each level (accuracy) | | See Acceptance Details, Below | |
| AC 3 | Recovered calibrator bottle values are within allowed recovered average % bias for all levels 2-5. | | | |
| AC 4 | Recovered calibrator bottle values are within allowed recovered SD at each level (precision) | xxxx | YYYY | |
| AC 5 | Recovered calibrator bottle values are within allowed recovered % cv at each level (precision) | xxxx | YYYY | |
| AC 6 | Slope of recovered bottle values versus actual is within allowed slope range | | See Acceptance Details, Below | |
| AC 7 | y-intercept of recovered bottle values versus actual is within allowed intercept range | | | |
| AC 8 | Correlation coefficient is within allowed correlation coefficient range. | xxxx | YYYY | |
| AC 9 | Δ instrument response between paired calibrator levels is within allowed Δinstrument response for each level pair, 1-2, 2-3, 3-4, 4-5 | | | |
| AC 10 | No QC flags associated with QC run in association with calibration. | | | |

Acceptance Details

| | AC 2, AC 3, AC 4, AC 5 | 1 | 2 | 3 | 4 | 5 | AC 9 | Allowed Δ | Actual Δ | Outcome |
|---|---|---|---|---|---|---|---|---|---|---|
| | Mean | 0.0 | 43.1 | 132.5 | 266.7 | 519.9 | Δ 1,2 | XXX | XXX | YYYY |
| | SD | 0.0 | 0.0 | 0.0 | 0.0 | 0.0 | Δ 2,3 | XXX | XXX | YYYY |
| | %CV | 0.0 | 0.0 | 0.0 | 0.0 | 0.0 | Δ 3,4 | XXX | XXX | YYYY |
| | Bottle Value | 0.0 | 42.9 | 133.2 | 266.7 | 522.6 | Δ 4,5 | XXX | XXX | YYYY |
| AC 2 | Allowed % Bias | XX.X | XX.X | XX.X | XX.X | XX.X | | | | |
| | Actual % Bias | V.V | V.V | V.V | V.V | V.V | | | | |
| | Outcome | | | | | | | | | |
| AC 3 | Allowed Ave. % Bias | XX.X | XX.X | XX.X | XX.X | XX.X | | | | |
| | Actual Ave. % Bias | V.V | V.V | V.V | V.V | V.V | | | | |
| | Outcome | | | | | | | | | |
| AC 4 | Allowed SD | XX.X | XX.X | XX.X | XX.X | XX.X | | | | |
| | Actual SD | V.V | V.V | V.V | V.V | V.V | | | | |
| | Outcome | | | | | | | | | |
| AC 5 | Allowed % CV | XX.X | XX.X | XX.X | XX.X | XX.X | | | | |
| | Actual % CV | V.V | V.V | V.V | V.V | V.V | | | | |
| | Outcome | | | | | | | | | |

FIG. 18

OPERATOR INTERFACE MODULE SEGMENTED BY FUNCTION IN AN AUTOMATIC CLINICAL ANALYZER

RELATED APPLICATION

This application claims the benefit of priority to Ser. No. 60/488,689 filed Jul. 18, 2003.

FIELD OF THE INVENTION

The present invention relates to a method for processing a patient's biological fluids in an automated clinical analyzer. In particular, the present invention provides a method for displaying the status and controlling the operation of such an analyzer on an operator interface in a manner that minimizes effort required by the operator to access pertinent data.

BACKGROUND OF THE INVENTION

Automated clinical analyzers are known to improve clinical analysis by providing results more rapidly while minimizing operator or technician error. Due to increasing demands on clinical laboratories regarding assay throughput, and the efficiency of handling patient samples and reagents An important factor is displaying the status and controlling the operation of such an analyzer in a "user friendly" manner that minimizes the effort required by the operator to access pertinent data.

Automated clinical analyzers are typically controlled by software executed by a computer using software programs written in a machine language like on the Dimension® clinical chemistry analyzer sold by Dade Behring Inc, of Deerfield, Ill., and widely used by those skilled in the art of computer-based electromechanical control programming. Such a computer executes application software programs for performing assays conducted by the analyzer but it is also required to be programmed to control and track, among other items:
- whether a reagent container is new and unused;
- calibration and quality control procedures as needed;
- an incoming and outgoing sample tube transport system;
- the patient's identity, the tests to be performed, if a sample aliquot is to be retained within the analyzer;
- the location of sample tubes, sample tube racks, and aliquot vessel arrays;
- a sampling probe;
- inventory and accessibility of sample aliquots within an environmental chamber;
- an aliquot vessel array transport system;
- reagent aspiration and dispense arms including liquid reagent probes;
- cuvette and vessel load stations;
- a wash station 67;
- a container shuttle, reagent carousels, shuttles and trays;
- reagent and assay chemical solution consumption along with time, and date of consumption of all reagents consumed out of each reagent container and assay chemical solutions consumed out of each vial container on a per reagent container, per calibration vial container, per Quality Control container, per assay, and per calibration basis, for specifically defined time periods; and,
- scheduling at least 1000 assays per hour.

From the above descriptions of the multiple operations conducted within a clinical analyzer, it is apparent that a complex problem to be resolved is how to display to a clinical analyzer operator or to an analyzer technician, on a user interface module, that information pertinent to a given situation, in a "user-friendly" manner.

U.S. Pat. No. 6,544,476 discloses a display screen having an area for indicating operation function selection buttons corresponding to respective groups of operation functions divided into a plurality of groups and an area for indicating an operation function screen corresponding to selected operation function selection buttons. The controller controls one of the operation function selection buttons, which corresponds to the plurality of groups allowed to access based on the level thus determined, to be accessible and also controls remaining one of the operation function selection buttons, which corresponds to remaining one of the plurality of groups having not been allowed to access, not to be accessible.

U.S. Pat. No. 6,275,150 discloses a user interface for a biomedical analyzer system that inputs work orders, including sample and test identifications, and transmits instructions to the instrument. The instrument performs the requested tests and sends the results to the computer, where they are stored. The test results are compared to exception review criteria to identify exception test results for operator review. Exception test results are also indicated by a graphic icon on the display of the computer. The exception test results may be compared by an operator to validation data gathered from the instrument and stored in the computer. The operator may then select a disposition for the exception test results. In another aspect of the present invention, alarm conditions are communicated by the instrument to the computer. The user interface then communicates the alarm conditions to an operator by using a graphic image of the instrument and an affected part. Additional information may then be provided to the operator by selecting the affected component.

U.S. Pat. No. 6,080,364 discloses an automatic analyzer in which a plurality of analytical units are arranged along a transfer line. This analyzer has a display request means for an inspection screen of calibration or accuracy management, a screen display for displaying an inspection screen having a plurality of classification captions installed in correspondence to classification of a plurality of states relating to calibration or accuracy management and an instruction button for instructing display of detailed information corresponding to each classification caption in association with the display request, and a controller for displaying, when an instruction is outputted by the instruction button, the analysis item name of the corresponding state and the analytical unit name for executing calibration or accuracy management of the corresponding analysis item on the inspection screen.

U.S. Pat. No. 5,885,530 discloses an automated immunoassay system which can perform testing on a broad range of analytes while selecting from among a range of different types of immunoassays using a variety of different types of reagents and immunoassay beads stored on-board the instrument. User interface is reduced as tests are performed automatically from computer input including the ability to order, perform and re-assay tests reflexively based on test results without operator intervention.

U.S. Pat. No. 5,316,726 discloses a computer controlled analyzer and display. The display provides a real-time presentation of all operations being performed within the analyzer. A large number of samples can be loaded into the analyzer, and the order of testing the samples can be rearranged according to a priority determined by the operator at any time. A variety of immunoassays can be performed on each sample and several different immunoassays can be performed on any one sample. Information related to the type of immunoassays being performed on particular samples is collected by a bar code reader and this information is conveyed to the computer for presentation on the display.

Japanese Patent Application 1-250758 proposes that an operator is allowed to use only the particular range of an analyzer's function corresponding to a pre-determined level. The operation functions of the automatic analyzer are classified into an analysis parameter, a system parameter, registration and maintenance, and the levels of the operators are set in accordance with identification codes of the respective operators in advance. When an operator inputs the identification code, only the operation function of the operation level corresponding to the inputted identification code is displayed. The levels of the operator are set as three levels of upper, middle and lower levels in a manner that the operator of the upper level is allowed to operate all the operations, the operator of the middle level is allowed to operate a part of the operations, and the operator of the lower level is allowed to operate only a part of the analysis parameter and the maintenance.

SUMMARY OF THE INVENTION

The present invention provides a method to display the status of a clinical analyzer on an operator interface in a manner that minimizes the effort required by the operator to access pertinent data by segmenting such data by function. This is achieved by providing a visual user interface device with a viewing screen that is adapted to display information pertaining to the control and operating status of the analyzer, segmenting the viewing screen so that routine operational information used in routine operation of the analyzer is displayed in a first segment of the viewing screen, and segmenting the viewing screen so that non-routine operational information that is used in a detailed examination of the operation of analyzer is displayed in a second segment of the viewing screen. In addition, an analyzer status summary tab is displayed in a first color if all operational systems within the analyzer are functioning within normal ranges, the color of the analyzer status summary tab is changed to a second color if any system or component within analyzer is beginning to approach a state that would cause analyzer to function outside a normal operating range, and the color of the analyzer status summary tab is changed to a third color range if any system or component within analyzer begins to function outside a normal operating range.

BRIEF DESCRIPTION OF THE DRAWINGS

The invention will be more fully understood from the following detailed description thereof taken in connection with the accompanying drawings which form a part of this application and in which:

FIGS. 10–13 are exemplary of routine operational information that is accessible from the screen of FIG. 9;

FIGS. 15–18 illustrates non-routine operational information accessible from the screen of FIG. 9;

FIGS. 21 and 22 illustrate actions to take based on the trouble-solving information of FIG. 20; and, FIG. 23 illustrates a personalized display screen exemplary of the present invention.

DETAILED DESCRIPTION OF THE INVENTION

Figure 1:
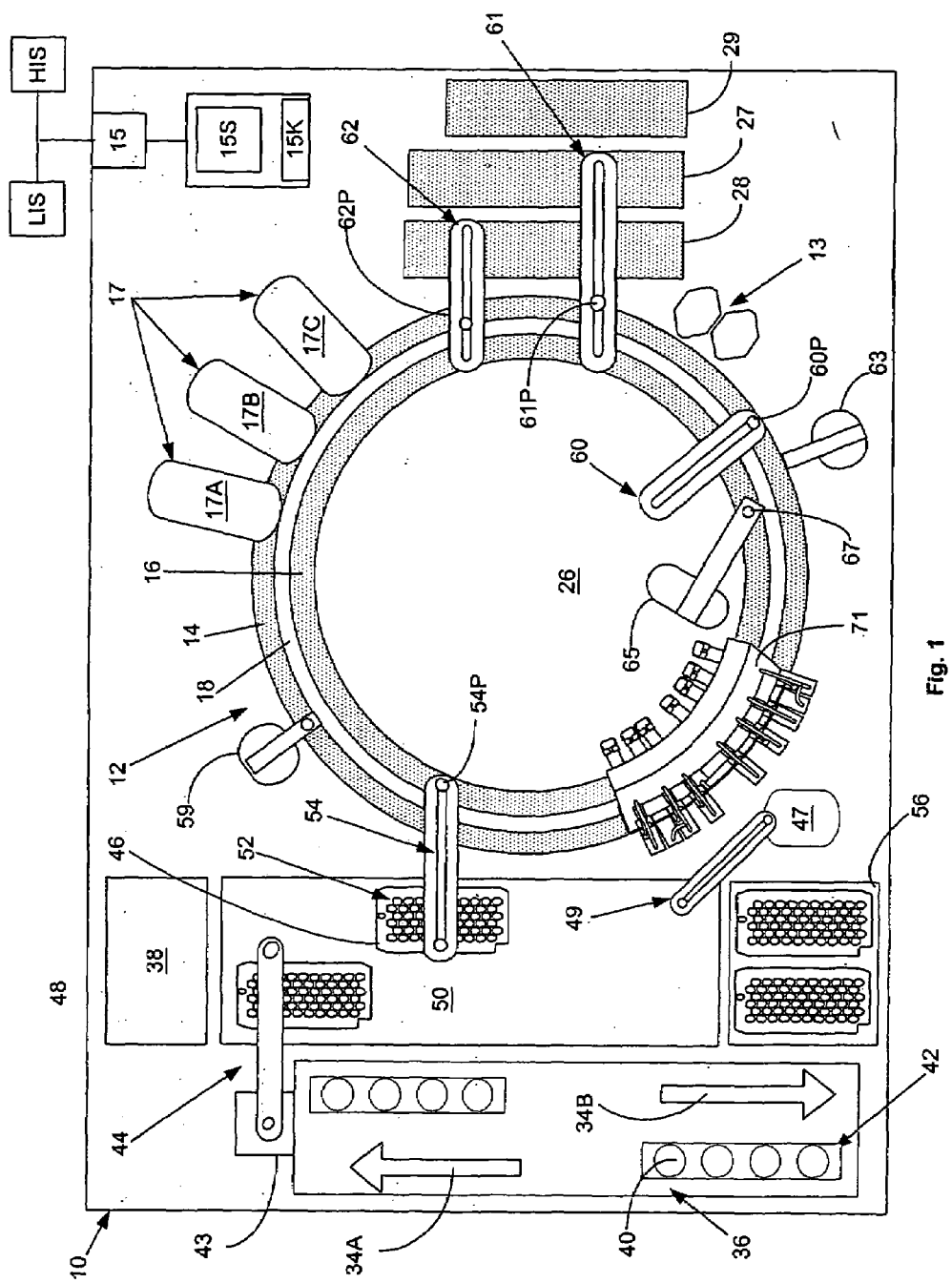
FIG. 1 is a schematic plan view of an automated analyzer in which the present invention may be employed to advantage.
Figure 2:
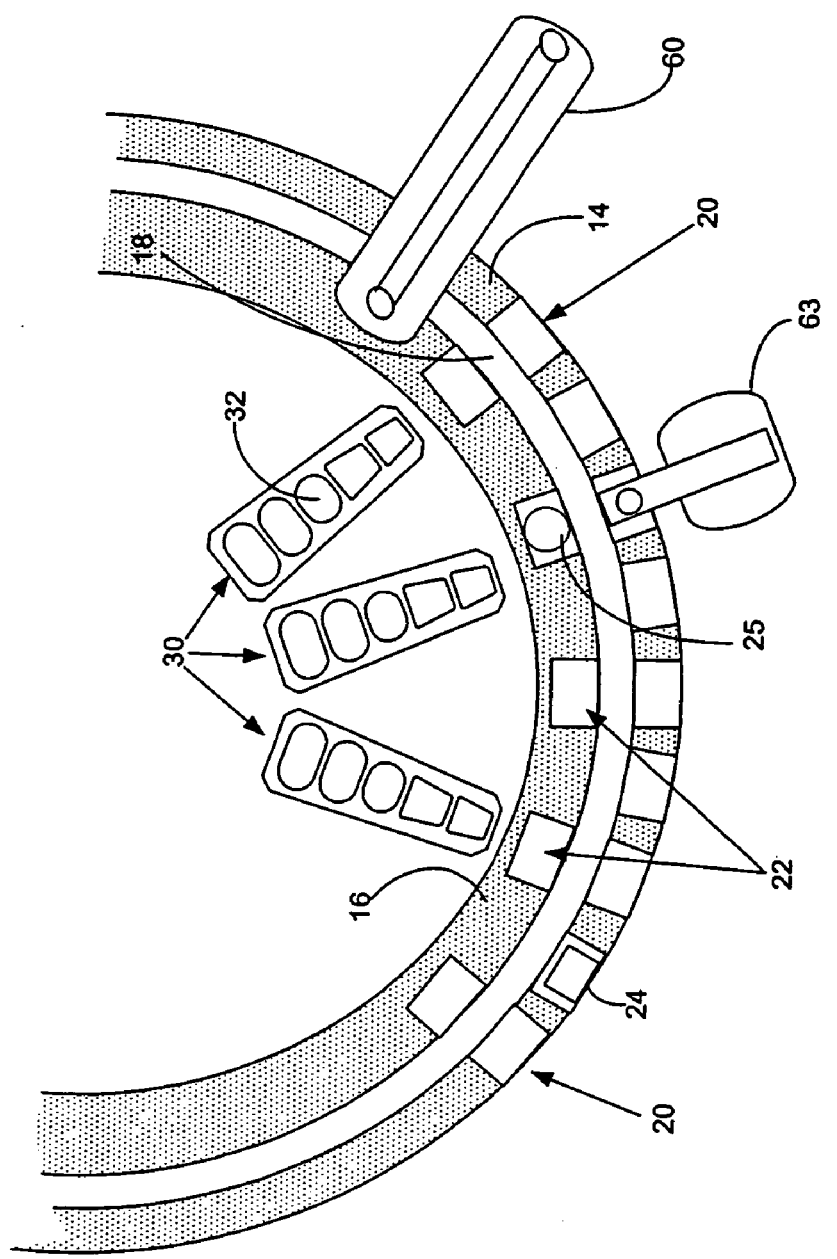
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 like disclosed in co-pending application Ser. No. 09/949,132 assigned to the assignee of the present invention and containing various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within cuvettes 24 and reaction vessels 25.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10. Analyzing means 17 may comprise analytical module 17A adapted to perform photometric assays, comprise analytical module 17B adapted to perform nephelometric assays, and comprise analytical module 17C adapted to perform luminescence assays, like disclosed in co-pending application Ser. No. 60/488,336 assigned to the assignee of the present invention. Computer 15 is interlinked using known interface software applications with a Laboratory Information System (LIS) and/or a Hospital Information System (HIS) so that information concerning patients, patient assay requests, assay results, analyzer status, and the like, may be immediately accessible as needed by laboratory personnel. Computer 15 includes an operator interface module 15M typically comprising a keyboard 15K and monitor or a flat-panel touch viewing screen 15S or the like, on which information about the operational status of analyzer 10 as described herein may be called up and displayed or which may be automatically displayed like in the instance of a malfunction within analyzer 10.

Figure 3:
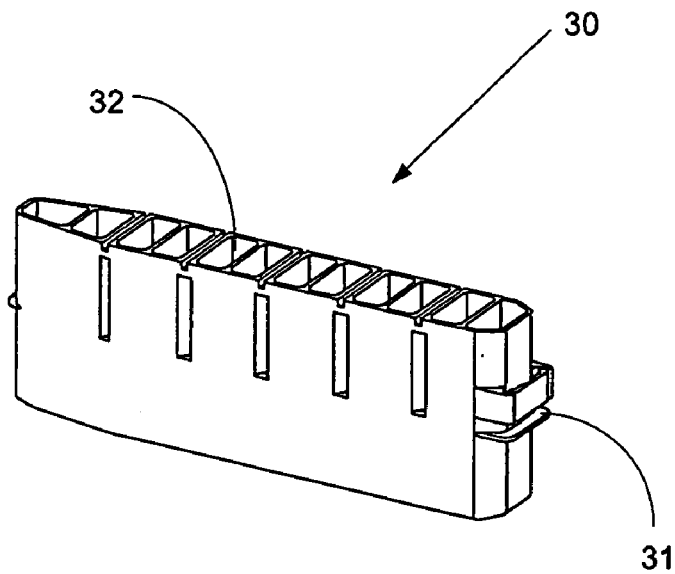
FIG. 3 is a perspective view of a reagent container useful in the analyzer of FIG. 1.
Figure 3A:
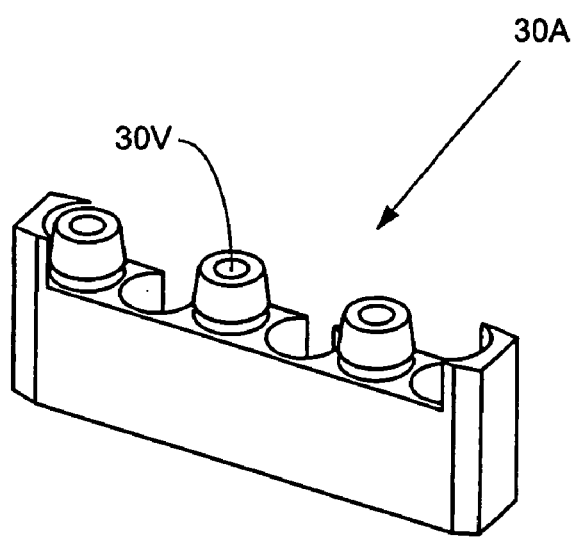
FIG. 3A is a perspective view of a calibration solution vial container useful in the analyzer of FIG. 1.

Temperature-controlled reagent storage areas 26, 27 and 28 store a plurality of multi-compartment elongate reagent containers 30 like that illustrated in FIG. 3A and containing reagents necessary to perform a given assay within a number of wells 32, each well containing as much as 3.4 mL of a given reagent. Container 30 has features to enable analyzer 10 to automatically determine whether a reagent container 30 is new and unused or whether the reagent container 30 has been previously used and possibly become contaminated whenever a reagent container 30 is initially placed onto an analyzer. FIG. 3B shows a calibration vial container 30A containing calibration solutions of known analyte concentrations in calibration solution vials 30V, the solutions being to conduct well-know calibration and quality control procedures within analyzer 10. Calibration vial containers 30A are also inventoried upon analyzer 10 within reagent storage areas 26, 27 and 28.

A bi-directional incoming and outgoing sample tube transport system 36 having input lane 34A and output lane 34B transports incoming individual sample tubes 40 containing liquid specimens to be tested and mounted in sample tube racks 42 into the sampling range of a liquid sampling probe 44, like disclosed in co-pending application Ser. No. 10/623,311 assigned to the assignee of the present invention. Liquid specimens contained in sample tubes 40 are identified by reading bar coded indicia placed thereon using a conventional bar code reader to determine, among other items, a patient's identity, tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 4:
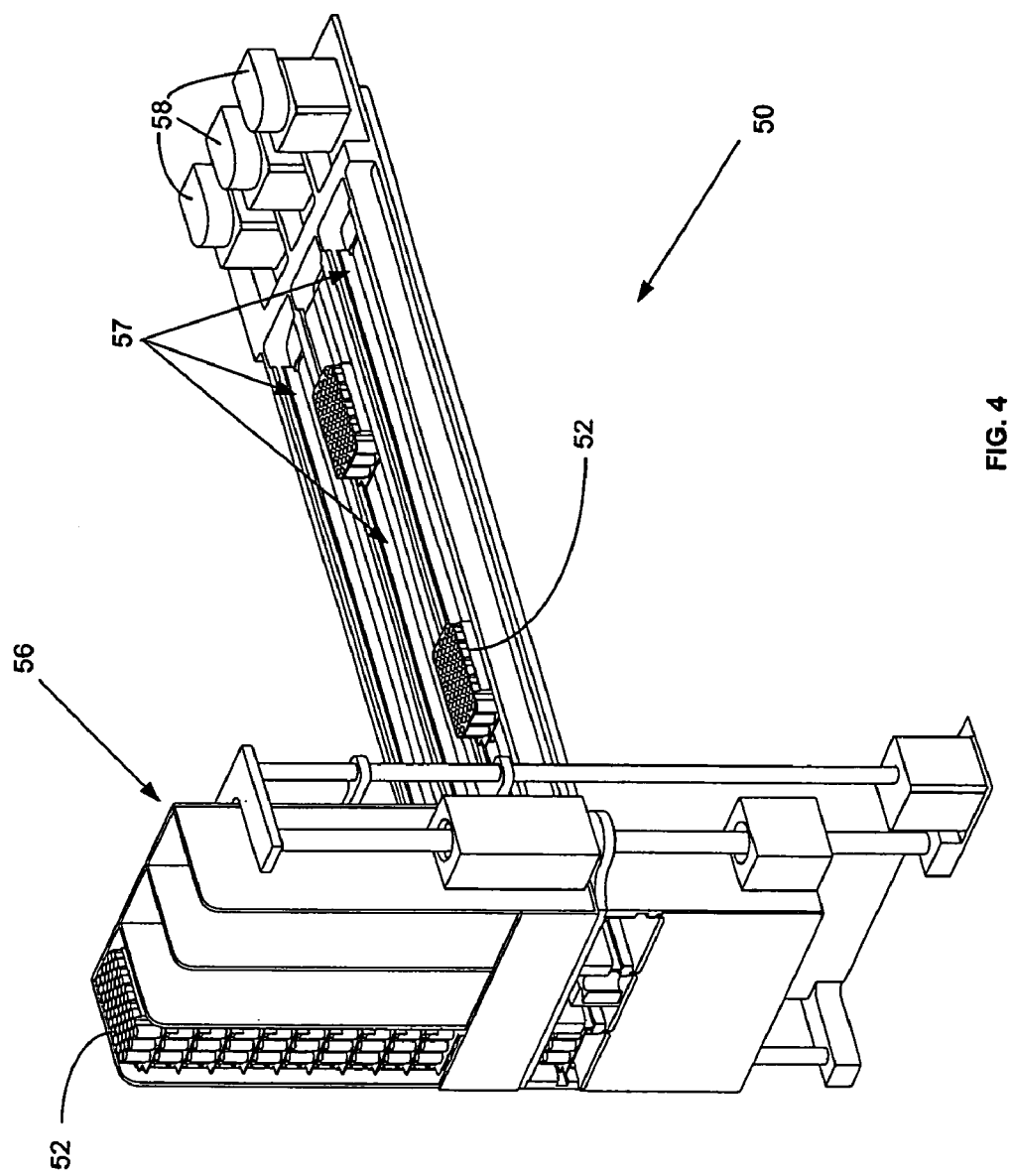
FIG. 4 is a perspective view of an aliquot vessel array storage and handling unit useful in the analyzer of FIG. 1.
Figure 4A:
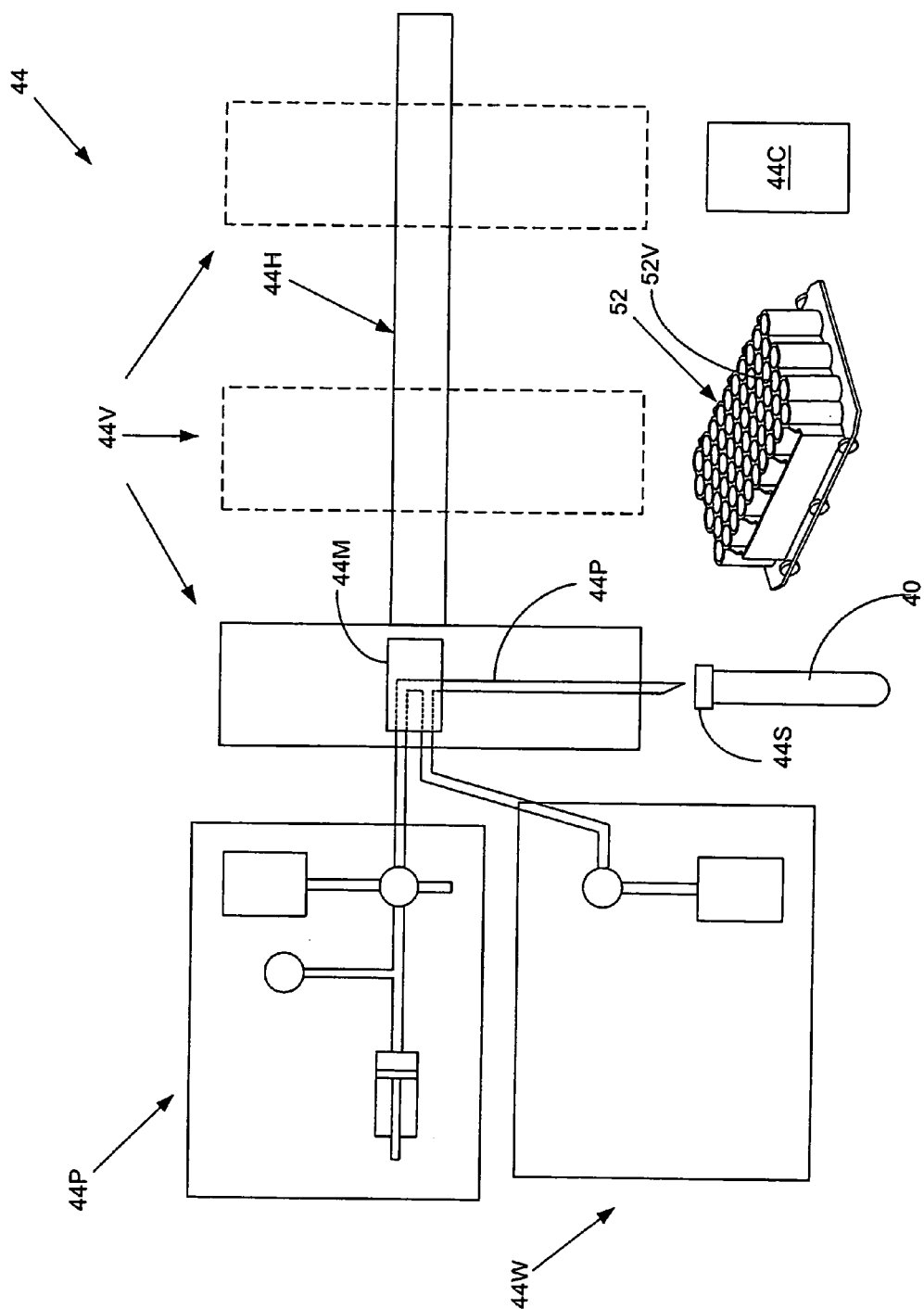
FIG. 4A is a sampling probe useful in the analyzer of FIG. 1.
Figure 5:
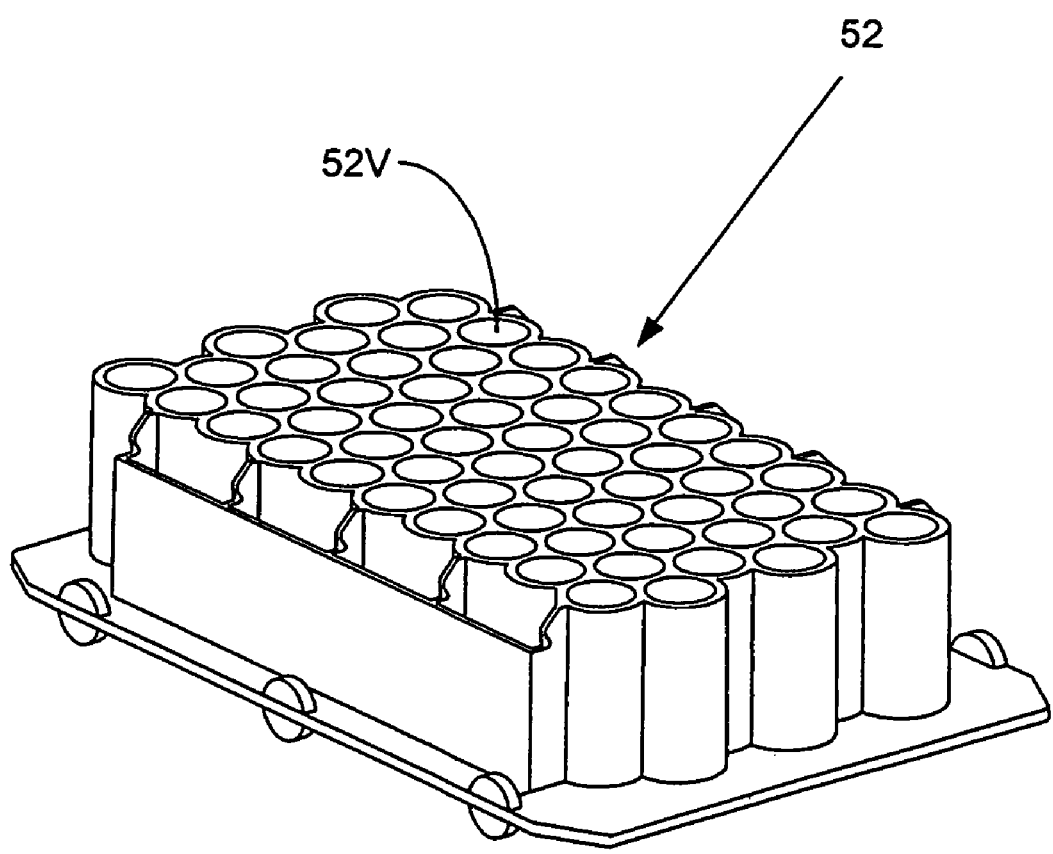
FIG. 5 is an aliquot vessel array useful in the analyzer of FIG. 1.

Sampling probe 44 comprises a translatable liquid sampling probe 48 so that movement of sampling arm 44 describes an arc intersecting the sample tube transport system 36 and an aliquot vessel array transport system 50, as seen in FIG. 4. Sampling probe 44, as seen in FIG. 4A, comprises a Horizontal Drive 44H, a Vertical Drive 44V, a Wash Module 44W, a Pump Module 44P and a Cleansing Module 44C having the primary functions described in Table 1 below, so that sampling probe 44 is operable to aspirate liquid sample from sample tubes 40 and to dispense an aliquot sample into one or more of a plurality of vessels 52V in aliquot vessel array 52, as seen in FIG. 5, depending on the quantity of sample required to perform the requisite assays and to also provide for a sample aliquot to be retained by analyzer 10 within environmental chamber 38.

TABLE 1

| Module | Primary Functions |
|---|---|
| Horizontal Drive 44 H | 1. Position Vertical Drive 44 V over sample fluid tubes 40 on a rack 38, over individual vessels 52 V of aliquot vessel arrays 52 and over Cleansing Module 44 C |
| Vertical Drive 44 V | 1. Position a sampling probe 44 P at vertical positions for aspiration and dispense operations |
| | 2. Drive probe 44 P through the stopper 40 S of a sample fluid tube 40 |
| | 3. Determine liquid level of sample fluid in sample tube 40 |
| | 4. Monitor aspiration quality |
| Wash Module 44 W | 1. Remove contamination from probe 44 C with liquid cleansing solutions |
| Cleansing Module 44 C | 1. Cleansing interior and exterior surfaces of sample fluid probe 44 P |
| Pump Module 44 P | 2. Aspirate and dispense sample fluid |
| | 3. Wash probe 44 P |
| Wash Manifold 44 M | 1. Connect Wash Module 44 W and Pump Module 44 P to probe 44 P |

Environmental chamber 38 is operated by computer 15 to ensure that the same patient specimen is tested a second time following a previous first testing. For reasons of processing efficiency, it is sometimes desirable to automatically reprocess a sample aliquot that has been retained in within environmental chamber 38 for a predetermined period of time. Incoming samples to be tested may be identified by bar coded indicia placed on sample tubes 40 to determine if a sample aliquot is to be retained, and if so, for what period of time. In addition to a first sample aliquot taken from a patient's specimen to be tested, a second sample aliquot is also taken from the same patient's specimen and is retained in within environmental chamber 38. If it becomes desirable to re-test or additionally test a patient's sample some period of time after tests on the first sample aliquot are completed, reported, and analyzed by a physician, the second sample aliquot may be quickly removed from within environmental chamber 38 and tested on analyzer 10, thereby saving time as well as providing for the exact same patient specimen to be tested.

A conventional ion selective electron measuring station 47 equipped with a conventional ion selective electron probe 49 may be conveniently located proximate aliquot vessel array transport system 50 in order to conduct ionic analyte measurements on sample aliquots aspirated from vessels 52V by probe 49 and dispensed into the ion selective electron measuring station 47.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and then liquid probe 54P is shuttled to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60, 61 and 62 each comprising at least one conventional liquid reagent probe, 60P, 61P and 62P, respectively, are independently mounted and translatable between reagent storage areas 26, 27 and 28, respectively. Probes 60P, 61P and 62P are conventional mechanisms for aspirating reagents required to conduct specified assays at a reagenting location from wells 32 in an appropriate reagent container 30, the probes 60P, 61P and 62P subsequently being shuttled to a reagent dispensing location where reagent(s) are dispensed into reaction cuvettes 24. Probes 60P, 61P and 62P are also used for aspirating calibration and control solutions from calibration solution vials 30V as required to conduct calibration and control procedures necessary to ensure proper operation of analyzer 10, the probes 60P, 61P and 62P subsequently being shuttled to a calibration solution dispensing location where solutions(s) are dispensed into reaction cuvettes 24 and analyzed by analyzing means 17.

Figure 4B:
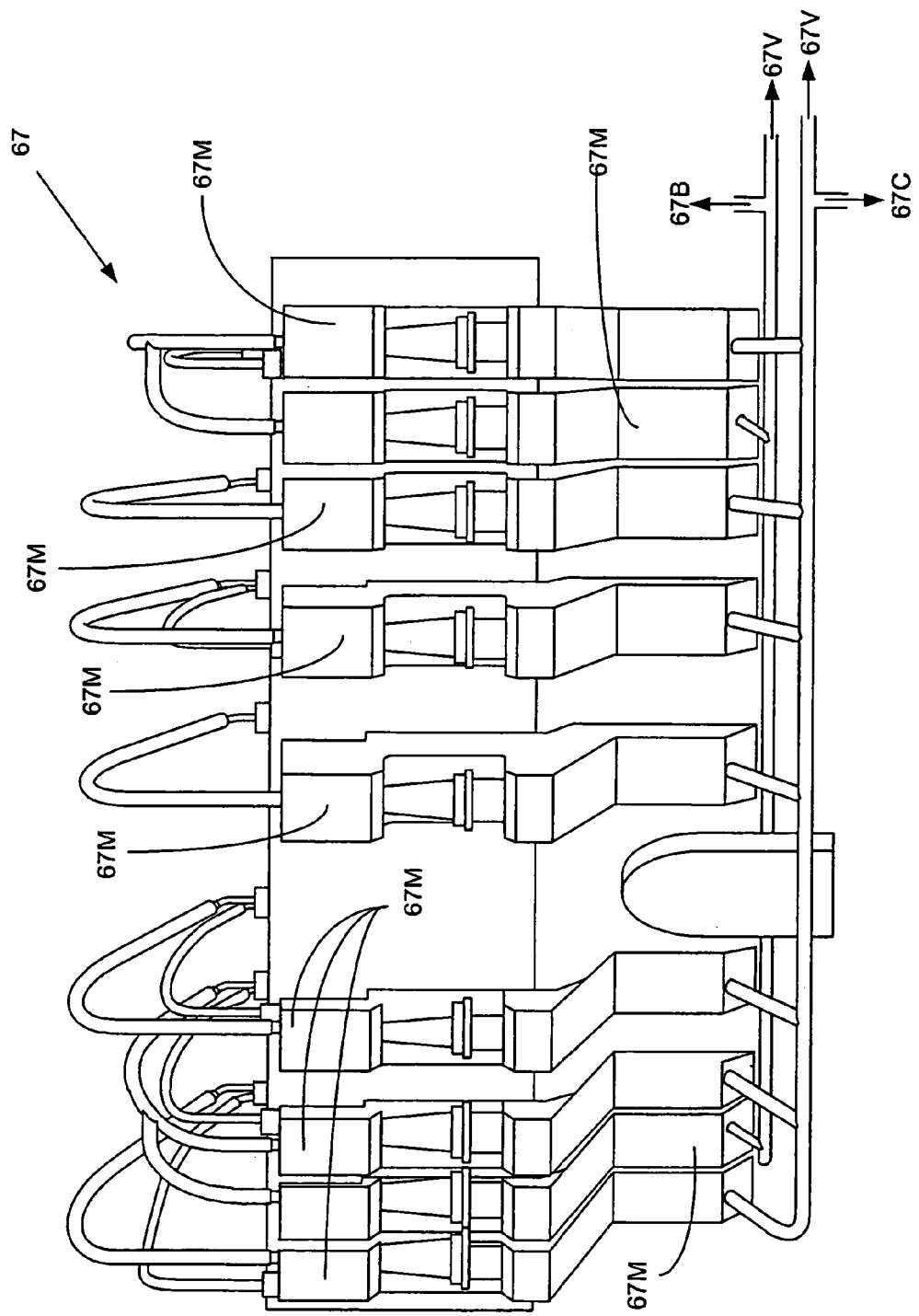
FIG. 4B is a wash station useful in the analyzer of FIG. 1.

Reaction cuvette load station 61 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a translatable robotic arm 65. In operation, used cuvettes 24 in which an assay has been finally conducted, are washed and dried in a wash station 67 like disclosed in co-pending application Ser. No. 10/623,360 assigned to the assignee of the present invention. Computer 15 operates wash station 67 so that a used reaction cuvette 24 is cleansed so that whenever certain "exceptional" assays are scheduled to be next performed in a reaction cuvette 24, the used reaction cuvette 24 is automatically subjected to an additional cleansing or cleaning operation, the terms "cleaning and cleansing" including washing, rinsing, and drying. This selective cleaning of a used reaction cuvette 24 is partially achieved by providing a number of washing and drying manifolds 67M, like seen in FIG. 4B, each of which is independently selectively activated to perform or not perform a cleansing operation, depending upon the identity of the assay scheduled to be next performed in that reaction cuvette 24. Further, wash station 67 is operated by computer 15 so that biohazard waste residues from biochemical reactions in a cuvette 24 are segregated from chemical waste residues from chemical reactions in a cuvette 24 and are safely disposed into secure biochemical waste storage 67B and chemical waste storage 67C by means of vacuum lines 67V.

Subsequent assays are conducted in cleaned used cuvettes 24 unless dictated otherwise for reasons like disclosed in co-pending application Ser. No. 10/318,804 assigned to the assignee of the present invention. Computer 15 is programmed to determine not to reuse a cleaned used reaction cuvette 24 whenever an assay scheduled to be next performed in a cleaned used reaction cuvette 24 might be adversely affected by any contaminants remaining from the assay previously performed in a cleaned used reaction cuvette 24. In addition, computer 15 may operate analyzer 10 so that whenever certain assays are scheduled to be next performed in a cleaned used reaction cuvette 24, the cleaned used reaction cuvette 24 is automatically removed, discarded, and replaced with a fresh, unused reaction cuvette 24. Computer 15 may optionally control analyzer 10 so that whenever an assay is scheduled to be next performed in a cleaned used reaction cuvette 24, and the same assay was previously performed in the cleaned used reaction cuvette 24 and the assay results were outside normal test ranges, the cleaned used reaction cuvette 24 would be automatically removed, discarded, and replaced with a fresh, unused reaction cuvette 24. Cuvette unload station 59 is adapted to remove unusable reaction cuvettes 24 from cuvette ports 20 again using a translatable robotic arm 65 like seen on load stations 61 and 63.

Figure 6:
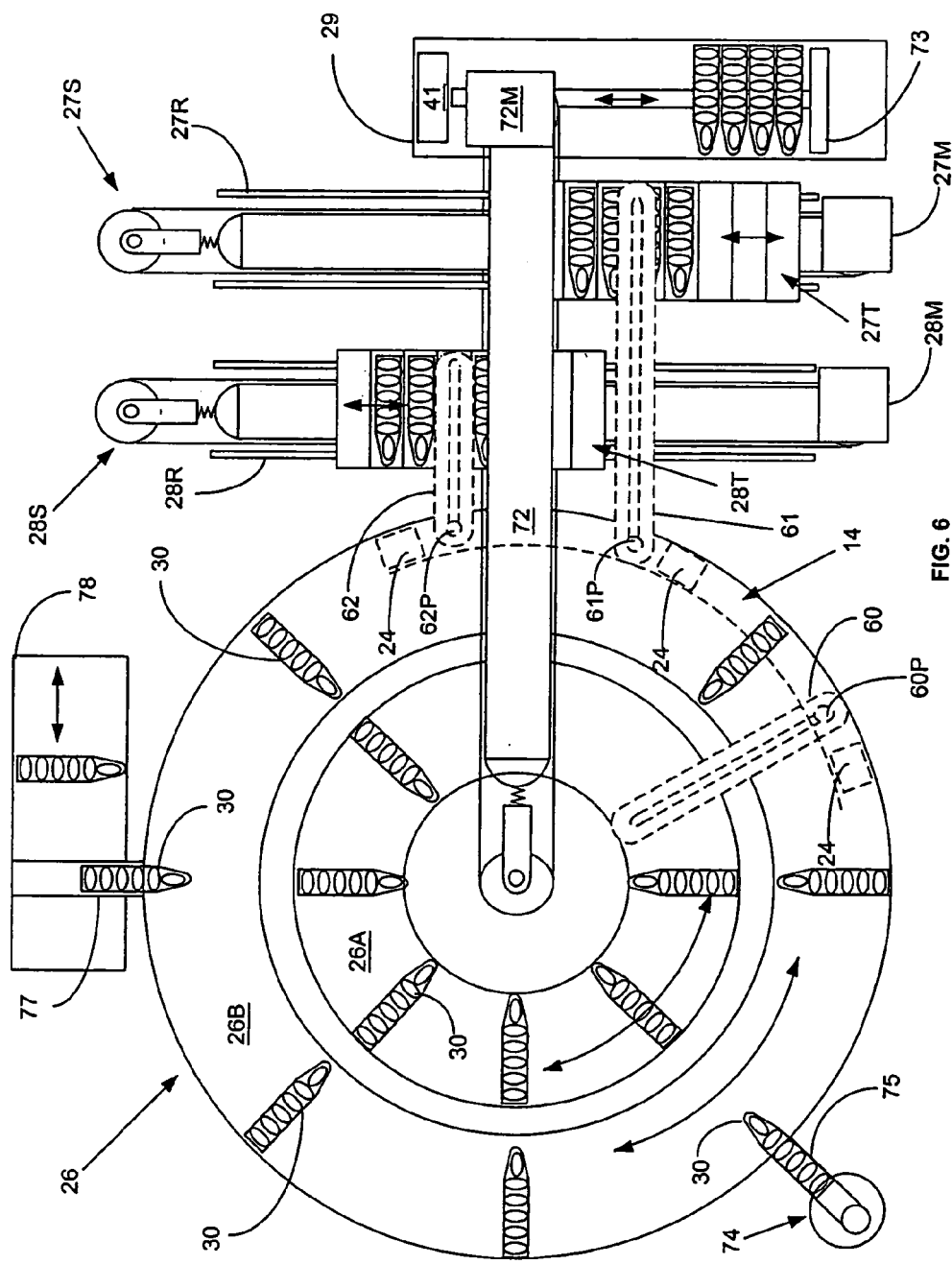
FIG. 6 is a schematic plan view of a container transport system useful in the analyzer of FIG. 1.

In order to re-supply assay reagents and calibration solutions as they are exhausted by assay demand, analyzer 10 includes a single, bi-directional linear container shuttle 72 illustrated in FIG. 6 and adapted to remove reagent containers 30 and calibration vial containers 30A from a container loading tray 29 having a motorized rake 73 that automatically locates containers 30 and 30A at a loading position beneath container shuttle 72. Shuttle 72 is further adapted to dispose a reagent container 30 or a calibration vial container 30A into slots in at least one slotted reagent container tray 27T or 28T within reagent storage areas 27 or 28, respectively. In a similar fashion, shuttle 72 is even further adapted to remove reagent containers 30 or calibration vial containers 30A from reagent container trays 27T and 28T and to dispose such reagent containers 30 or calibration vial containers 30A into either of two concentric reagent carousels 26A and 26B within reagent storage area 26. Shuttle 72 is also adapted to move reagent containers 30 and calibration vial containers 30A between the two concentric reagent carousels 26A and 26B. As indicated by the double-headed arc-shaped arrows, reagent carousel 26A may be rotated in both directions so as to place any particular one of the reagent containers 30 or calibration vial containers 30A disposed thereon beneath reagent aspiration arm 60. Although reagent carousel 26B may also contain reagent containers 30 and calibration vial containers 30A accessible by reagent aspiration arms 60 and 62, carousel 26B is preferably designated only for storing excess inventory of reagent containers 30 and calibration vial containers 30A. Any one of the reagent containers 30 disposed in reagent container trays 27T and 28T may be located at a loading position beneath container shuttle 72 or at a reagent aspiration location beneath aspiration and dispensing arms 61 and 62, respectively, by reagent container shuttles 27S and 28S within reagent storage areas 27 and 28, respectively. Reagent aspiration arms 60 and 62 are shown in dashed lines to indicate that they are positioned above the surfaces of reagent containers 30 inventoried in carousel 26B, and reagent container trays 27T and 28T, respectively. Reaction cuvettes 24 supported in outer cuvette carousel 14 are also both shown in dashed lines to indicate that they are positioned above the surfaces of reagent containers 30. FIG. 6 also shows a reagent preparation station 74 connected to reagent operation carousel 26B by means of a first reagent container transfer device 75. Reagent preparation station 74 is adapted to perform a number of reagent preparation operations like chemical additions, re-mixing, hydrating dry reagent powders and the like as may be required. In addition, a motorized belt shuttle 78 connected to reagent operation carousel 26B by means of a second reagent container transfer device 77, thereby enabling an exchange of reagent containers 30 between similarly equipped analyzers. A container shuttle system like seen in FIG. 6, is described in co-pending U.S. patent Ser. No. 10/623,310, assigned to the assignee of the present invention.

Figure 7:
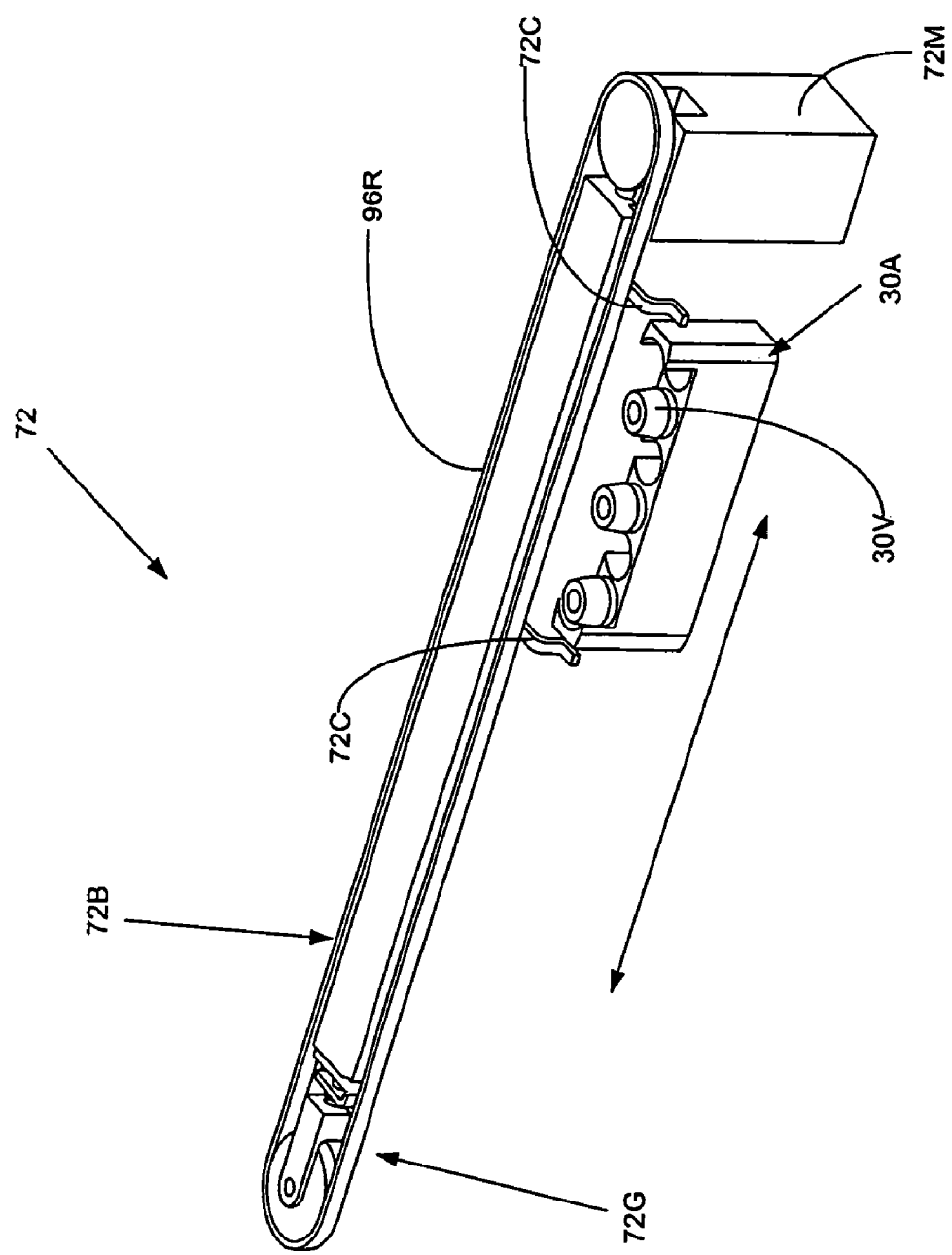
FIG. 7 is a perspective view of a container shuttle useful in the analyzer of FIG. 1.
Figure 8:
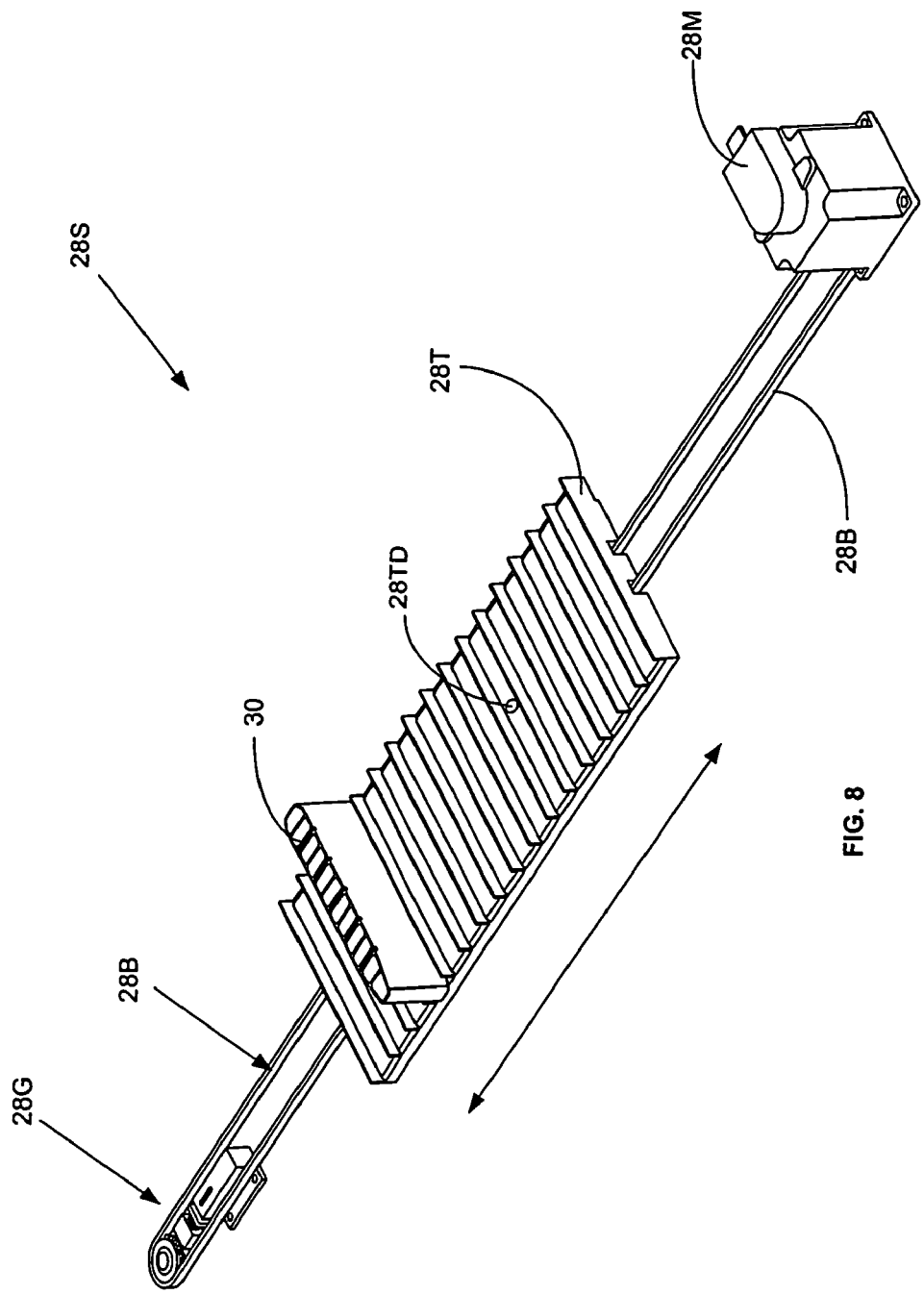
FIG. 8 is a perspective view of a container tray shuttle useful in the analyzer of FIG. 1.

Container shuttle seen in FIG. 7 is adapted to automatically compensate for unknown changes in length of a drive belt 72B driven by motor 72M by an automated tensioner 72T, disclosed in co-pending application Ser. No. 10/623,311 and assigned to the assignee of the present invention, and adapted to maintain a constant tension on the drive belt 72B regardless of rapid changes in its driving direction so that reagent containers 30 and calibration vial containers 30A attached thereto by clamps 72C may be accurately positioned along the direction of drive belt 72B, as indicated by the double-ended arrow, and disposed at their intended location beneath reagent container shuttle 72 or within storage areas 26, 27 or 28 as drive belt 72B wears. Reagent container shuttles 27S and 28S are similar in design to one another, and as seen in FIG. 8, include a reagent container tray 28T secured to one leg of a drive belt 28B so that tray 28T is free to be driven to and from along the direction of drive belt 28B, as indicated by the double-ended arrow. Consequently, reagent containers 30 within slots in tray 28T may be automatically positioned at a pick-up location beneath container shuttle 72.

From the preceding description of analyzer 10, it is clear to one skilled in the art that the capabilities of analyzer 10 under the control of computer 15 include the ability to automatically to move reagent containers 30 and calibration vial containers 30A between container loading tray 29, reagent container trays 27T and 28T, and reagent carousels 26A and 26B. By means of shuttles 27S and 28S, analyzer 10 is further capable of moving reagent containers 30 and calibration vial containers in reagent container trays 27T and 28T to appropriate aspiration locations by probes 61P and 62P, respectively, (or to a loading location beneath shuttle 72) so that in combination with the capability of reagent carousels 26A and 26B to place any reagent container 30 or calibration vial container 30A beneath reagent aspiration arms 60P, 61P and 62P. Analyzer 10 thus includes an automated random access reagent and calibration solution re-supply system with the flexibility to position a large number of different reagents and calibration solutions at different aspiration locations.

A key factor in maintaining an optimum assay throughput within analyzer 10 is the ability to timely re-supply reagent containers 30 into reagent storage areas 26, 27 and 28 before the reagents contained therein become exhausted. Similarly important is the ability to timely re-supply calibration and Quality Control solutions in vial containers 30A before the solutions contained therein become exhausted so that calibration and control procedures may be conducted as required, whether this be based on the basis of time between calibrations or number of assays performed since an immediately previous calibration or number of assay results outside normal ranges, or changes in the performance of the analyzer. This challenge may be met by timely equipping analyzer 10 with additional requisite calibration and Quality Control solutions used in calibration and control procedures and called standard chemical solutions herein for convenience, before they become exhausted, thereby maintaining assay throughput of analyzer 10 uninterrupted.

In order to maintain continuity of assay throughput, computer 15 is programmed to track reagent and assay chemical solution consumption along with time, and date of consumption of all reagents consumed out of each reagent container 30 and assay chemical solutions consumed out of each vial container 30A on a per reagent container, per calibration vial container, per Quality Control container, per assay, and per calibration basis, for specifically defined time periods. As disclosed in co-pending application Ser. No. 10/622,435 and assigned to the assignee of the present invention, computer 15 is programmed to make an inventory demand analysis for specifically defined time periods so as to determine future assay inventory demands for the specifically defined time periods and display to an operator on an operator interface module 15D, a list of all of the reagent containers 30 and calibration/Quality Control vial containers 30A that will be needed in the future in a timely manner prior to the actual need of said reagent container 30 and calibration/Quality Control vial containers 30A.

A very simplified illustration of the analysis made by computer 15 may be found in Table 1, wherein an average assay demand is conducted on Monday, using the most recent historical Tuesday-specific assay demand for the four previous Tuesdays, for Total CO2, Creatinine, and BUN is 1255, 1140, and 1050, respectively. In view of the number of assays that may be conducted in single different reagent containers 30 containing the reagents needed to perform Total CO2, Creatinine, and BUN assays, and considering the on-board inventory of the different reagent containers 30 as indicated, it is clear that one additional reagent container 30 for Total CO2 is needed for Tuesday and that two additional reagent containers 30 for Creatinine and BUN are needed for Tuesday. This information is displayed on computer display module 15M so that the requisite different reagent containers 30 may be timely supplied into tray 29 of analyzer and shuttled throughout analyzer 10 as required by a container transport system like seen in FIG. 6 in order to maintain a continuous throughput within analyzer 10.

TABLE 2

| Assays Per Reagent Container 30 | Assay Type | Averaged Assay Demand | Reagent Containers 30 on Analyzer 10 | Additional Reagent Containers 30 Needed on Analyzer 10 |
|---|---|---|---|---|
| 540 | Total CO2 | 1255 | 2 | 1 |
| 450 | Creatinine | 1140 | 1 | 2 |
| 480 | BUN | 1050 | 1 | 2 |

As known in the art, an analyzer like analyzer 10 is not limited to the three assays in Table 1, and instead is typically adapted to perform as many as 180–200 different assays, with the reagents required to perform about 50% of these "on-board assays" always on-board analyzer 10 in storage areas 26, 27 and 28. In an exemplary embodiment of analyzer 10, in order to improve assay throughput, the reagent containers 30 containing reagents required to perform all "on-board assays" would be held in storage area 26 while the reagent containers 30 containing reagents required to perform less frequently requested all "on-board assays" might be divided between storage areas 27 and 28. When operated in this manner, about 250–500 assays per hour may be scheduled by computer 15 using reagent containers 30 held in storage area 26, while about 500 assays per hour may be scheduled by computer 15 using reagent containers 30 held in each of storage areas 27 and 28, so that computer 15 is scheduling between 1,250 to 1,500 assays per hour. These assay throughput values do not include about 375 ionic analyte measurements for sodium, potassium and chloride additionally performed by ion selective electron measuring station 47 on about 125 different samples per hour in aliquot vessel wells 52V.

Throughput values like those just described may be achieved because during operation of analyzer 10 by computer 15, different incoming samples 40 for which different assays are to be performed are partitioned into a number of separate assay groups in accord with the length of time required for the assay to be completed on reaction carousel 14, disclosed in co-pending application Ser. No. 10/151,424 and assigned to the assignee of the present invention. Judicious partitioning of assays by time, taken with carefully designed dwell times, number of reaction vessels 24, and location of assay devices 13 enables a first medium time length assay and a second shorter time length assay to be completed in less than a single operational cycle, thereby increasing the analyzer's 10 volume throughput as compared to conventional analyzers in which a reaction mixture having been analyzed may remain on a reaction carousel for an unproductive time period of inactivity. In particular, during a single full operational cycle of reaction carousel 14, medium length time assays are first completed within a number of reaction vessels 24; as each medium length time assay is completed, those reaction vessels 24 are removed from reaction carousel 14 and are replaced by new or cleaned reaction vessels 24 in which shorter length time assays are then completed. Longer length time assays remain on reaction carousel 14 during a full operational cycle.

From the above description of analyzer 10, computer 15 is required to be programmed to control, among other items:
analytical modules 17A, 17B, 17C;
determine whether a reagent container 30 is new and unused;
to conduct well-know calibration and quality control procedures as needed;
incoming and outgoing sample tube transport system 36;
patient's identity, the tests to be performed, if a sample aliquot is to be retained within analyzer 10;
control and track the location of sample tubes 40, sample tube racks 42, and aliquot vessel arrays 52;
operation of sampling probe 44;
inventory and accessibility of sample aliquots within environmental chamber 38;
ion selective electron probe 49 and ion selective electron measuring station 47;
aliquot vessel array transport system 50;
reagent aspiration and dispense arms 60, 61 and 62 including liquid reagent probes 60P, 61P and 62P;
reaction cuvette load station 61 and reaction vessel load station 63;
wash station 67;
linear container shuttle 72, reagent carousels 26A and 26B, shuttles 27S and 28S, reagent container trays 27T and 28T;
tracking reagent and assay chemical solution consumption along with time, and date of consumption of all reagents consumed out of each reagent container 30 and assay chemical solutions consumed out of each vial container 30A on a per reagent container, per calibration vial container, per Quality Control container, per assay, and per calibration basis, for specifically defined time periods; and,
scheduling between 1,250 to 1,500 assays per hour.

Clearly, from the above descriptions of the multiple operations conducted within analyzer 10 as controlled by computer 15, it is apparent that a complex problem to be resolved is how to display to a clinical laboratory operator or to an analyzer technician on display module 15M, that information pertinent to a given situation, in a "user-friendly" manner.

A key feature of the present invention is to segment the viewing screen 15S of display module 15M so that a significant portion, and preferably, a majority of the viewing screen 15S displays routine operational information that is used in routine operation of analyzer 10. In the preferred embodiment shown, at least 90% of the viewing screen 15S displays routine operational information that is used in routine operation of analyzer 10. Routine operational information includes, for example, information about entering a sample order, checking on the status of a sample being analyzed, reading sample results, reading a list of the reagent containers 30 and calibration/Quality Control vial containers 30A needed to be loaded into tray 29 the next day, and the like. In contrast, less than 10% of the viewing screen 15S displays non-routine or advanced operational information that is used in a detailed examination of information concerning the operation of analyzer 10. Advanced operational information includes, for example, information about which reagent container 30 lot is being used to currently perform each of the different assays analyzer 10 is equipped to perform, the expiration dates of each of the reagent lots, the calibration status of each of the reagent lots, a relative comparison of calibration coefficients between a new and a previous calibration, what are the existing calibration acceptance criteria, and the like.

Figure 9:
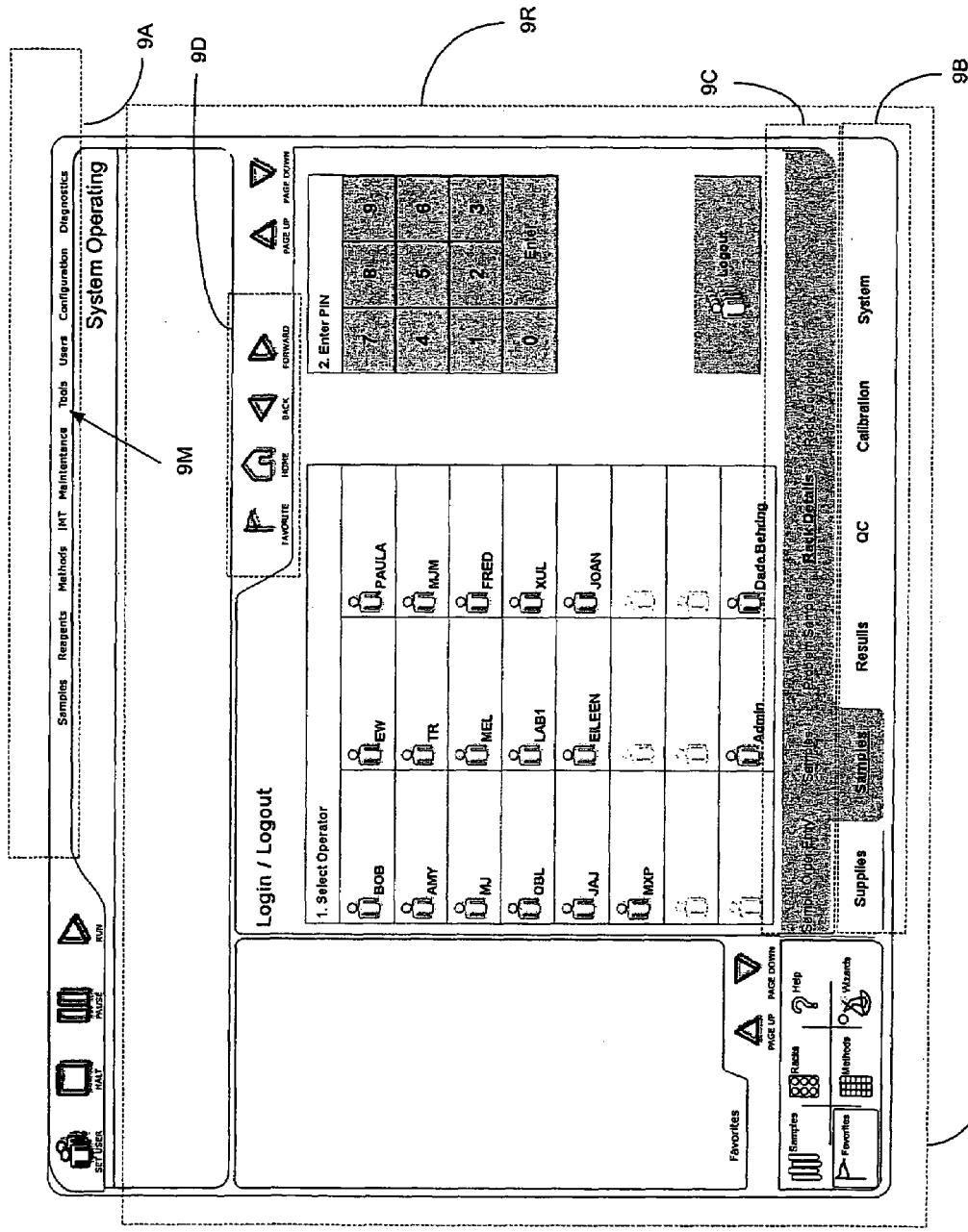
FIG. 9 is a viewing screen exemplary of the present invention.
Figure 9A:
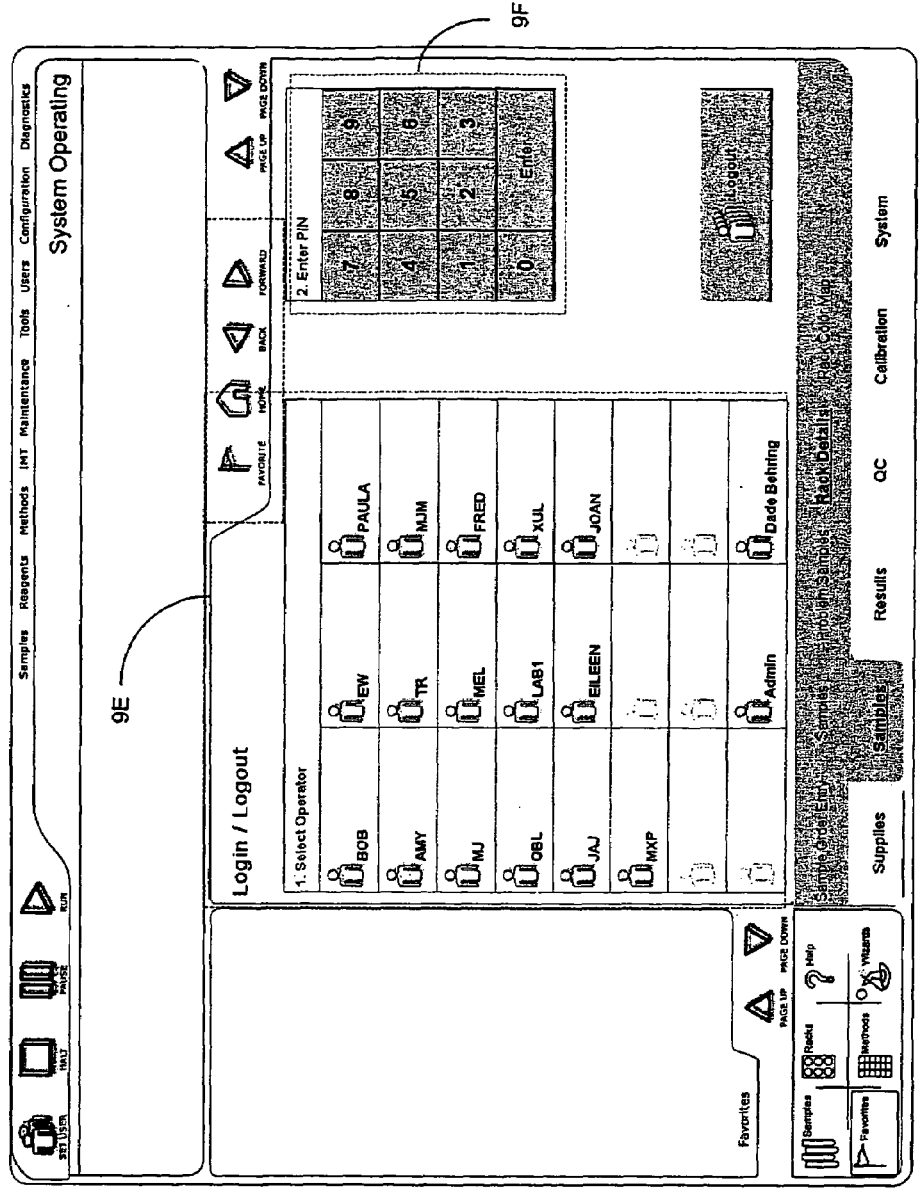
FIG. 9A illustrates access to display screens exemplary of the present invention.

FIG. 9 is an example of viewing screen 15S in which the routine operational information occupies the lower, greater than 90% of screen 15S, identified as 9R and this information is easily accessed using only the tab rows 9B and 9C at the bottom of screen 15S and the Home/Back/Forward buttons 9D. FIG. 9 is exemplary of the present invention whereby computer 15 is programmed to structure screen 15S on an operator specific basis so that a routine user cannot stumble into complexity that they are unable to handle. This structuring has implications in documentation and training programs, and also makes it much easier to train an operator to accomplish the essential functions required to maintain continuous throughput in analyzer 10, without needing to provide extensive overall operational knowledge. In contrast, prior art systems have been structured "by function", in which for example, all the complexity of calibration, is displayed in the same screen space. The routine operator was faced with the same functions available to the highly qualified and trained operator but did not have the training to address those issues. The routine screens exemplary of the present invention do not require a routine operator to even be aware of the complex, non-routine operational aspects of maintaining throughput of analyzer 10. If a problem arises, an alert is displayed, and the routine operator is taken where they need to go to resolve the issue, and the tools to accomplish it are close at hand. The routine screens display simple information and it is very difficult, if not impossible, to make an error, like destroy the store's inventory by pushing the wrong button. There is an advanced mode interface, which is available to highly trained and qualified technicians knowledgeable in the all of the non-routine aspects of a clinical chemistry system. A login/Logout area 9D may be seen in FIG. 9A where both routine operators and qualified technicians having been trained in non-routine, advanced aspects of operating analyzer 10 may gain access to linked screens after sequentially touching a Personal Information Number in area 9E. Only a relatively few linked information screens are in 9C, about 5 in each category in 9B. Active buttons in area 9R are touch-activated. FIGS. 10–13 described next are only exemplary of the routine operational information that is used in routine operation of analyzer 10 and are not intended to be exhaustive. For convenience reasons only, dashed lines are used in FIGS. 9–13 to indicate areas within screen 15S.

Figure 10:
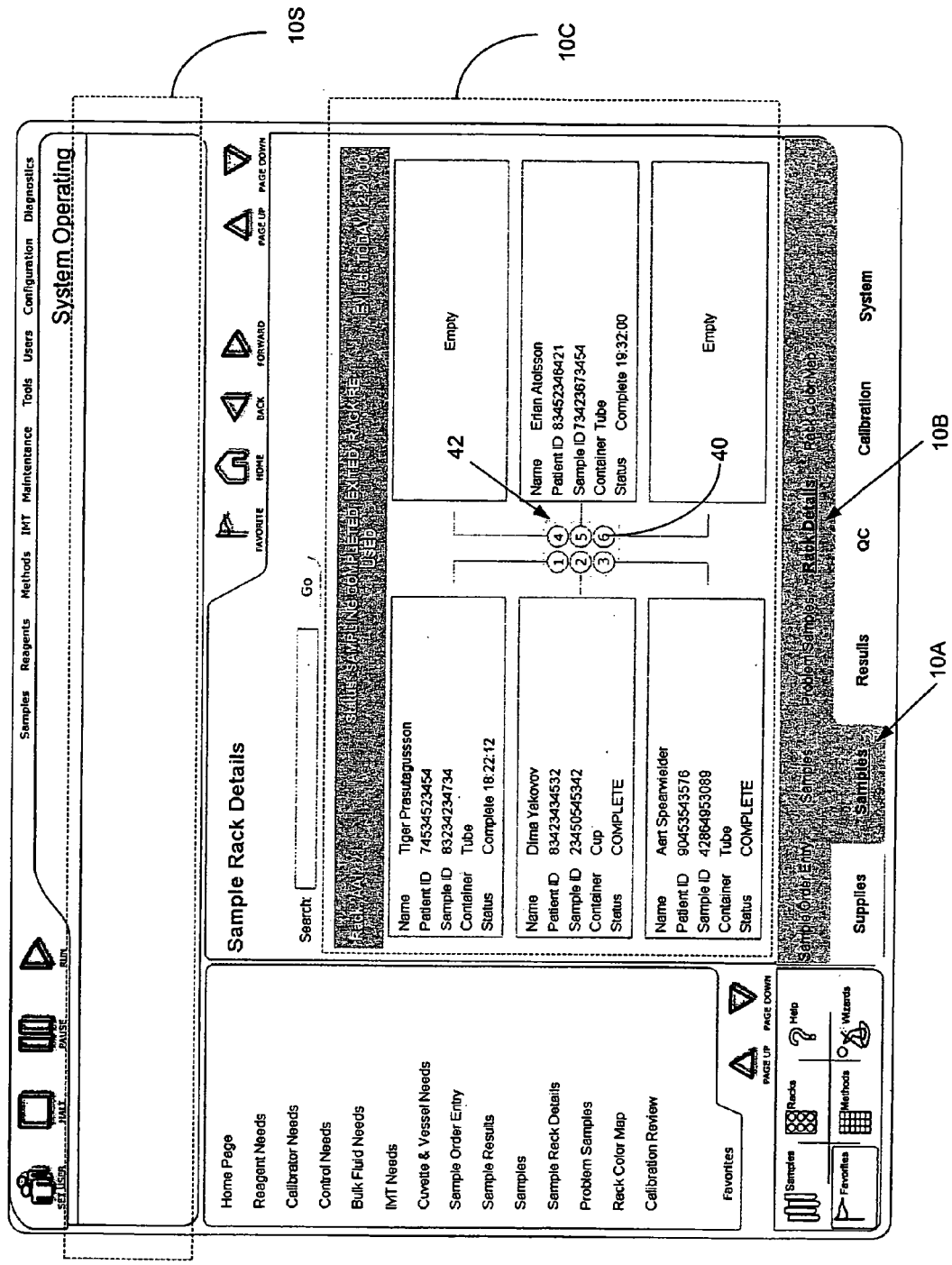

FIG. 10 is an example of a Sample Rack Detail screen accessed by touching Sample button 10A and then Rack Details button 10B. The status of sample tubes 40 on sample rack 42 is displayed for each sample tube 40 in status display area 10C. FIG. 10 also illustrates another important feature of the present invention being an Instrument Status Summary tab 10S described later.

Figure 11:
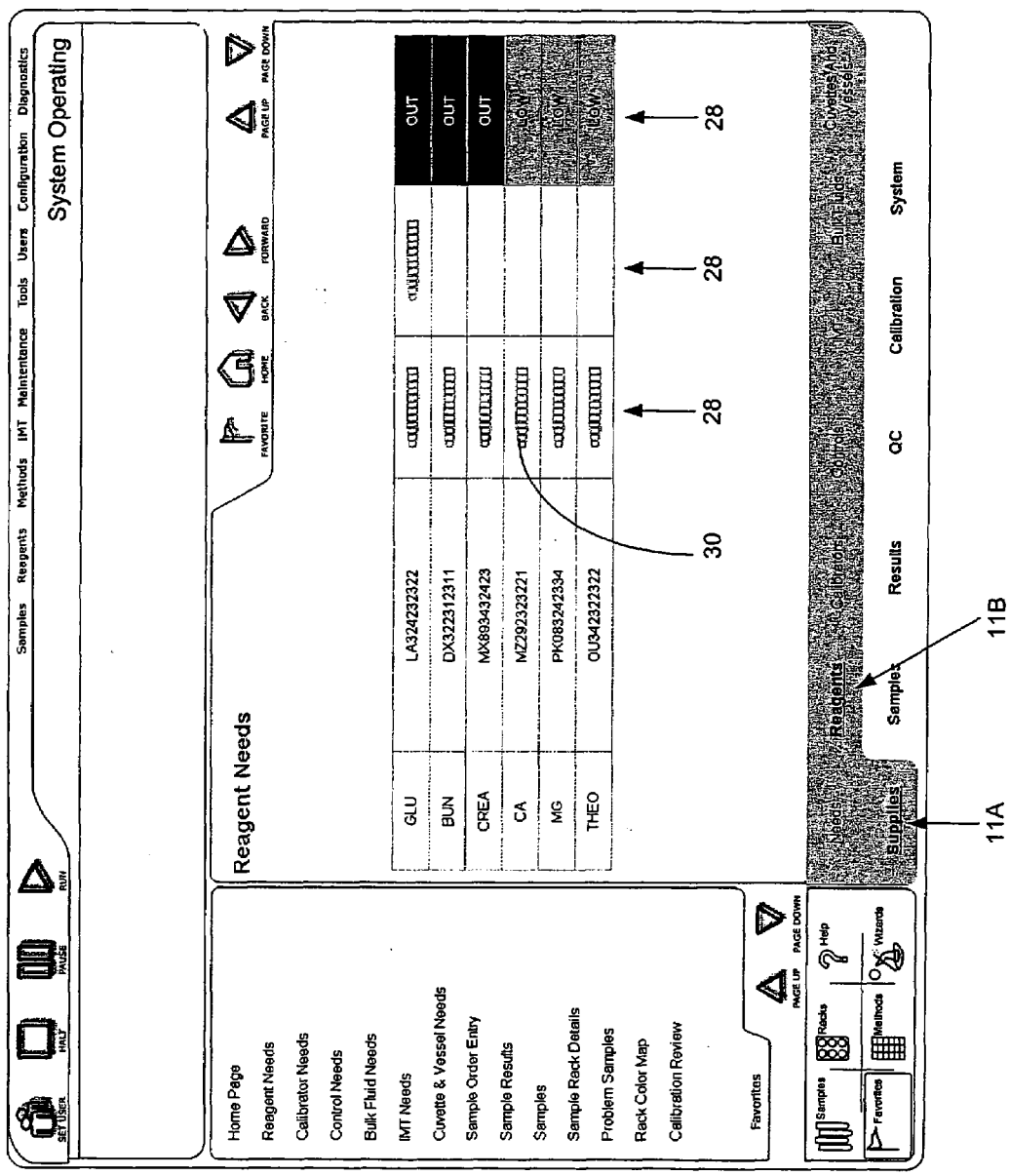

FIG. 11 is an example of a Reagent Needs screen accessed by touching Supplies button 11A and then Reagents button 11B. The status of reagent carriers 30 within storage areas 26, 2, and 28 is displayed for each of the assays currently being processed, for example.

Figure 12:
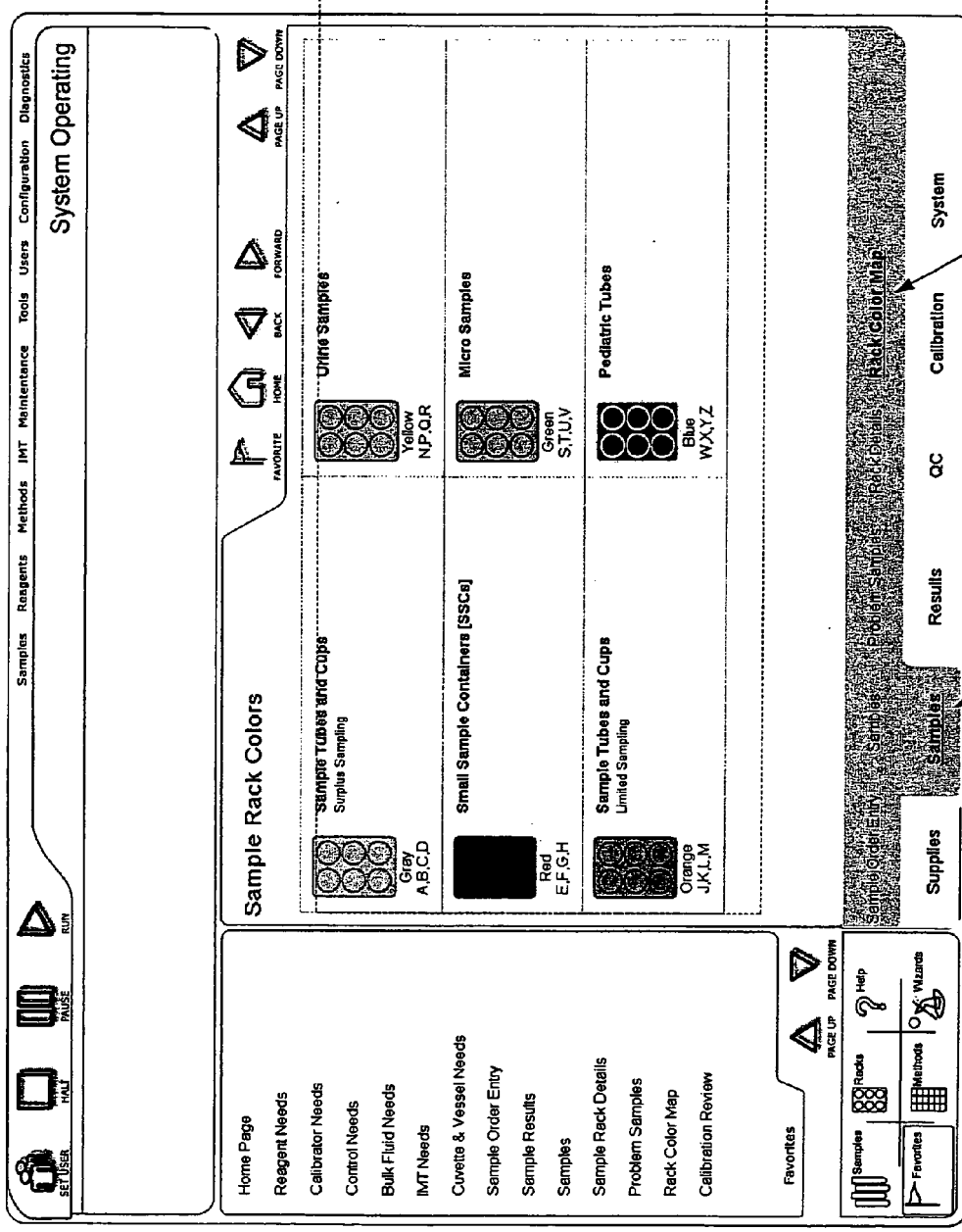

FIG. 12 is an example of a Sample Rack Colors screen accessed by touching Samples 12A and then Rack Color Map button 12B. Coloring rack 42 assists in distinguishing sample tubes 40, as illustrated in the information display area 12C and also allows an operator to approve aspirating additional sample for storage in environmental chamber 38 for follow on testing. Each rack color is designated to hold a particular type of sample tube 40, fluid type, or used to designate that surplus sampling is allowable. All racks 42 have a barcode, and an association between rack color and rack barcode is set up by the operator. So, in effect, computer 15 and the operator both 'know'" what the color is. When the operator loads a tube 40, he is careful to put the correct container/fluid/surplus in the correct rack 42. It is important that pediatric tubes be distinguished from normal tubes to order to avoid driving probe 66 through the bottom of a pediatric sample tube.

Figure 13:
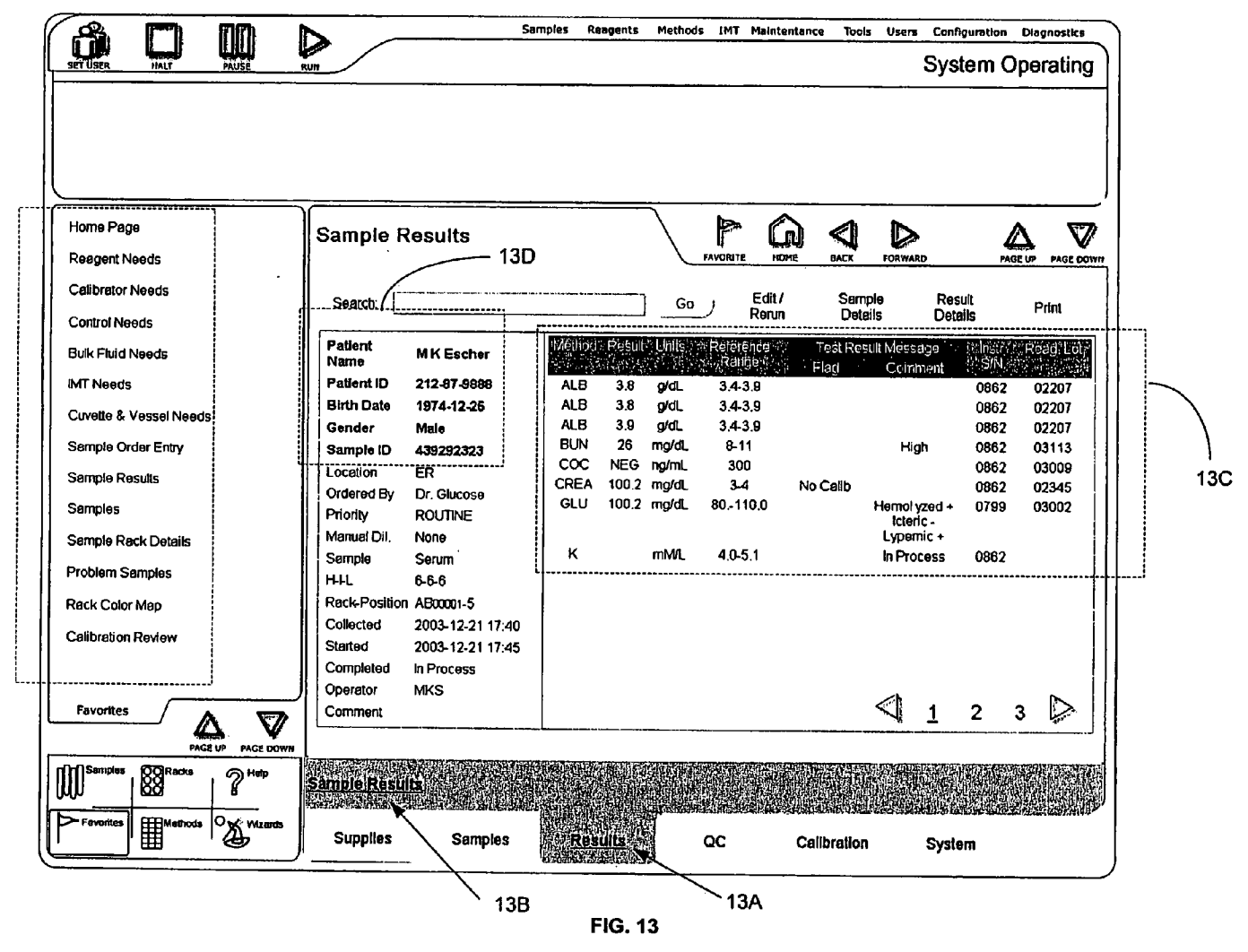

FIG. 13 is an example of a Sample Results screen accessed by touching Results button 12A and then Sample Results button 12B. Information concerning test results for various assays is available in area 13C for a patient identified in area 13D.

FIG. 9 also illustrates how the advanced operational information occupies the remaining, upper, and less than 10% of viewing area of screen 15S, identified as 9A. Advanced operational information screens, generally addressed with a hand-mouse, are accessed using the advanced menu 9M at the top right. The advanced information screens are dense component based screens, which appear in independent windows, not in the content area of the main screen 15S. Advanced information screens include Calibrator and QC setup, database maintenance and administration, diagnostics brought up as a separate task, user administration, method setup, open channels, sample carrier color assignment, reagent auto-preparation configuration, and the like as illustrated in FIGS. 14–17.

Figure 14:
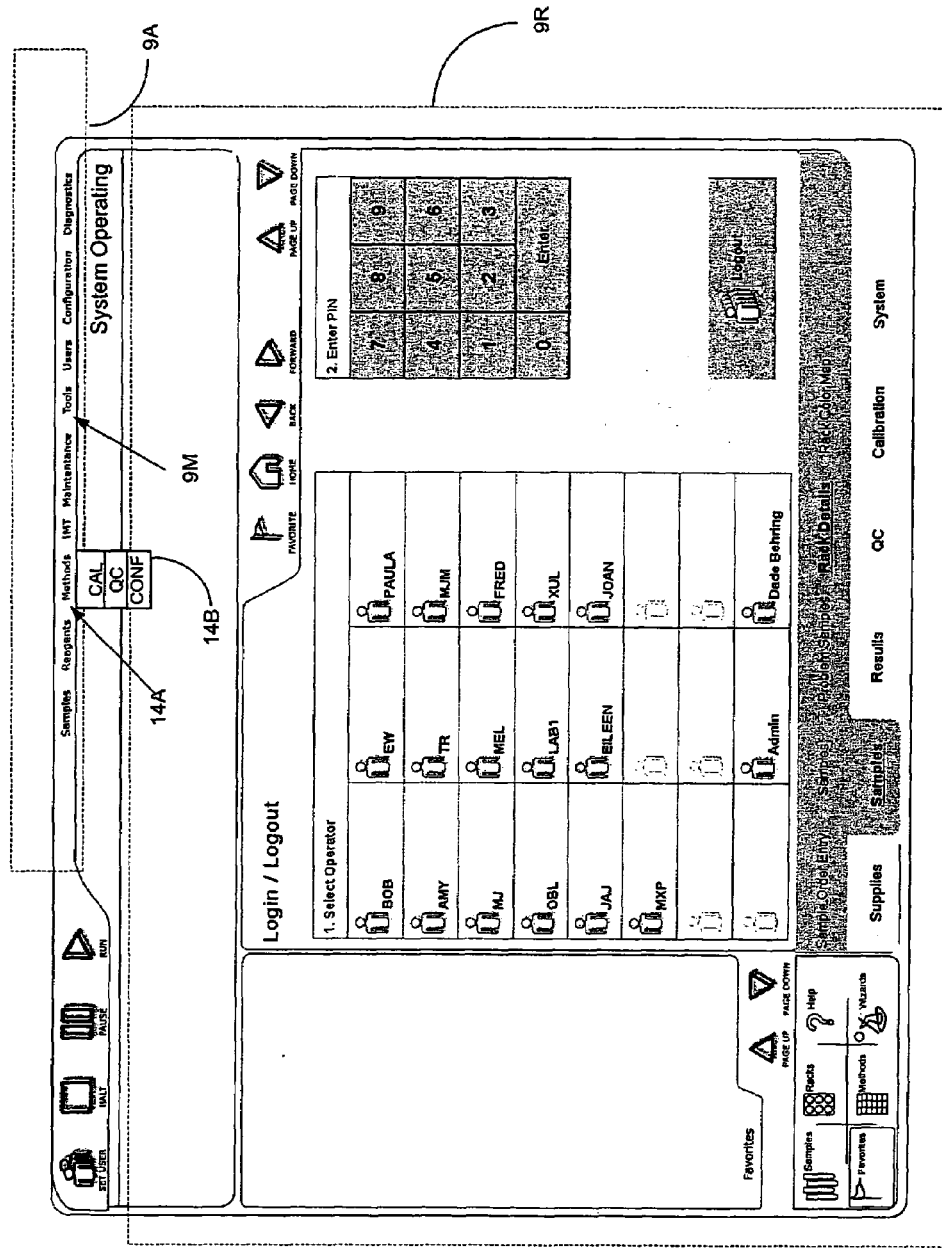
FIG. 14 illustrates how non-routine operational information is accessible from the screen of FIG. 9.

FIG. 14 illustrates how dense, advanced information is accessed in advanced operational information screens, FIGS. 15–18, by qualified personnel after conventionally logging in with an approved PIN. Using a mouse or keyboard, due to the smallness of menu 9M, access to assay-related method information is initiated by activating "Methods 12A" after which a pop-up menu 12B appears.

To obtain advanced information about calibration, for example, the qualified person selects CAL in menu 14B, from which screens containing advanced information are caused to be displayed on screen 15S by computer 15.

Figure 15:
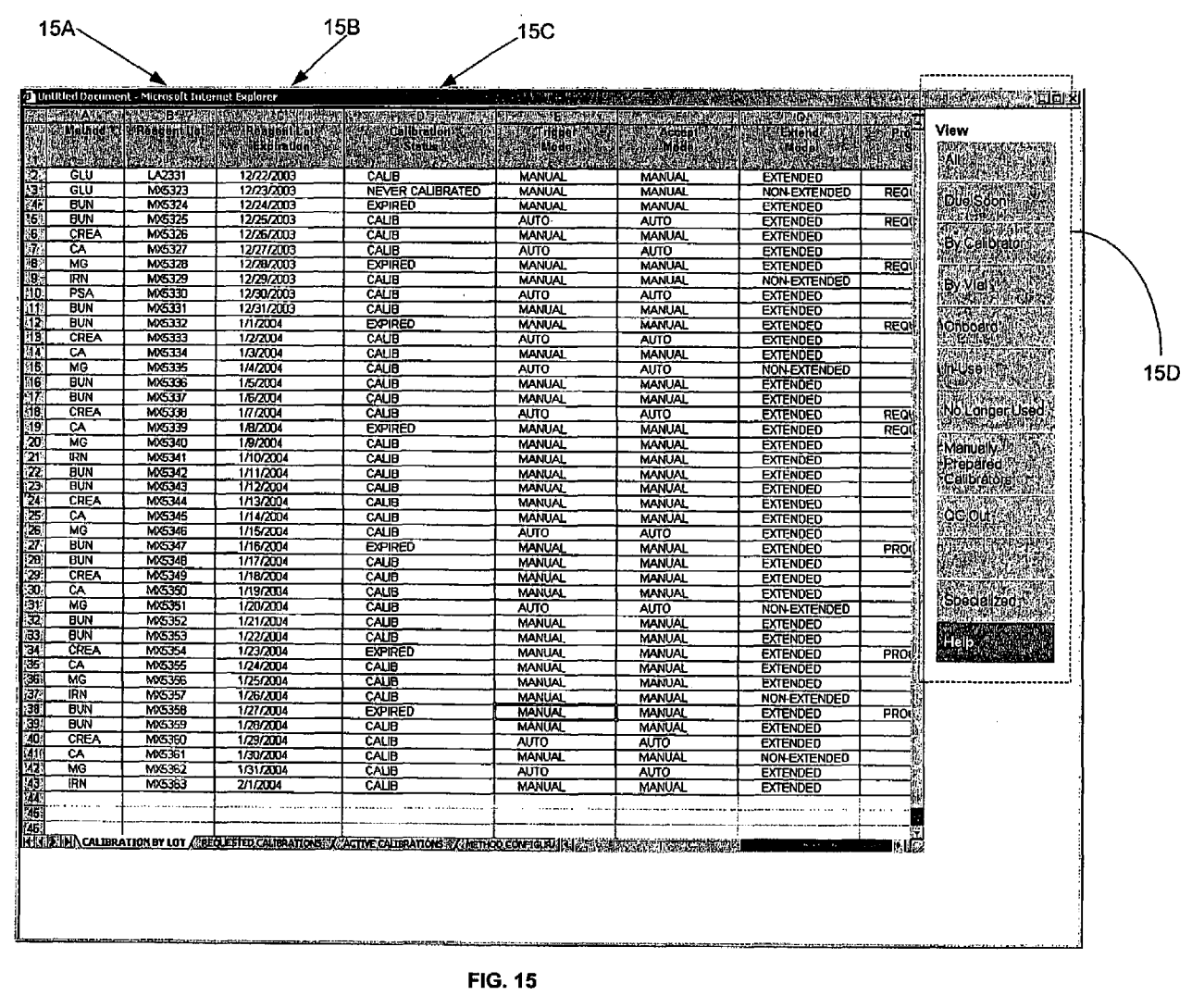

FIG. 15 is an example of a screen having densely detailed and advanced information about assay calibration by reagent lot 15A, including expiration date 15B and calibration status 15C. Additional calibration information like which re-calibrations are due soon, or are already on-board analyzer 10 may be obtained by activating the appropriate portion of area 15D.

Figure 16:
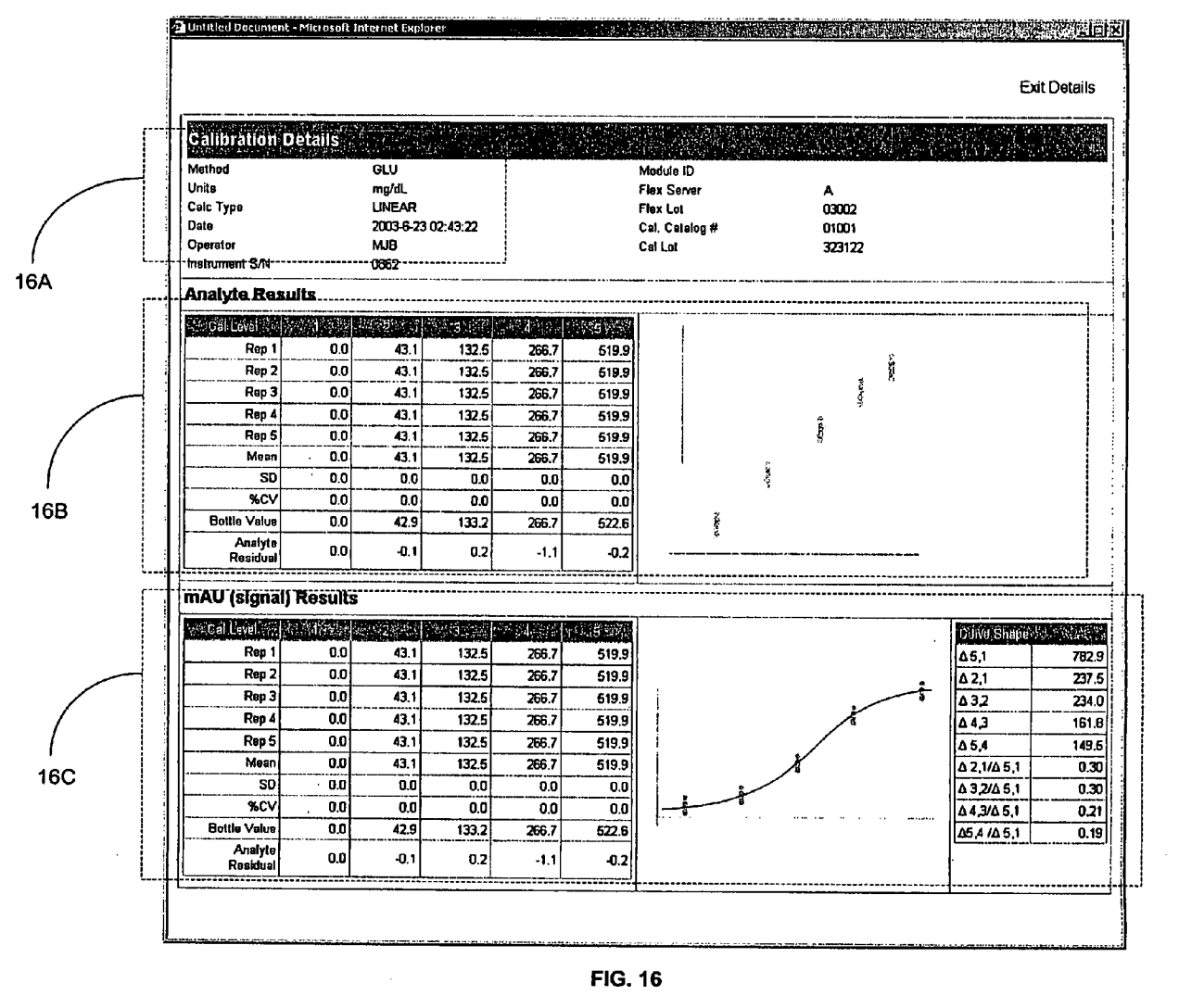

FIG. 16 is an example of a screen having densely detailed and advanced information about assay calibration details, including information about the date a particular method was calibrated by which operator by which type of calibration as seen in area 16A. The actual results of the calibration process may be found in area 16B covering analyte test results and in area 16C covering actual calibration signal results. This type of advanced information would normally be accessed except by highly qualified personnel, for example in a trouble-shooting activity.

Figure 17:
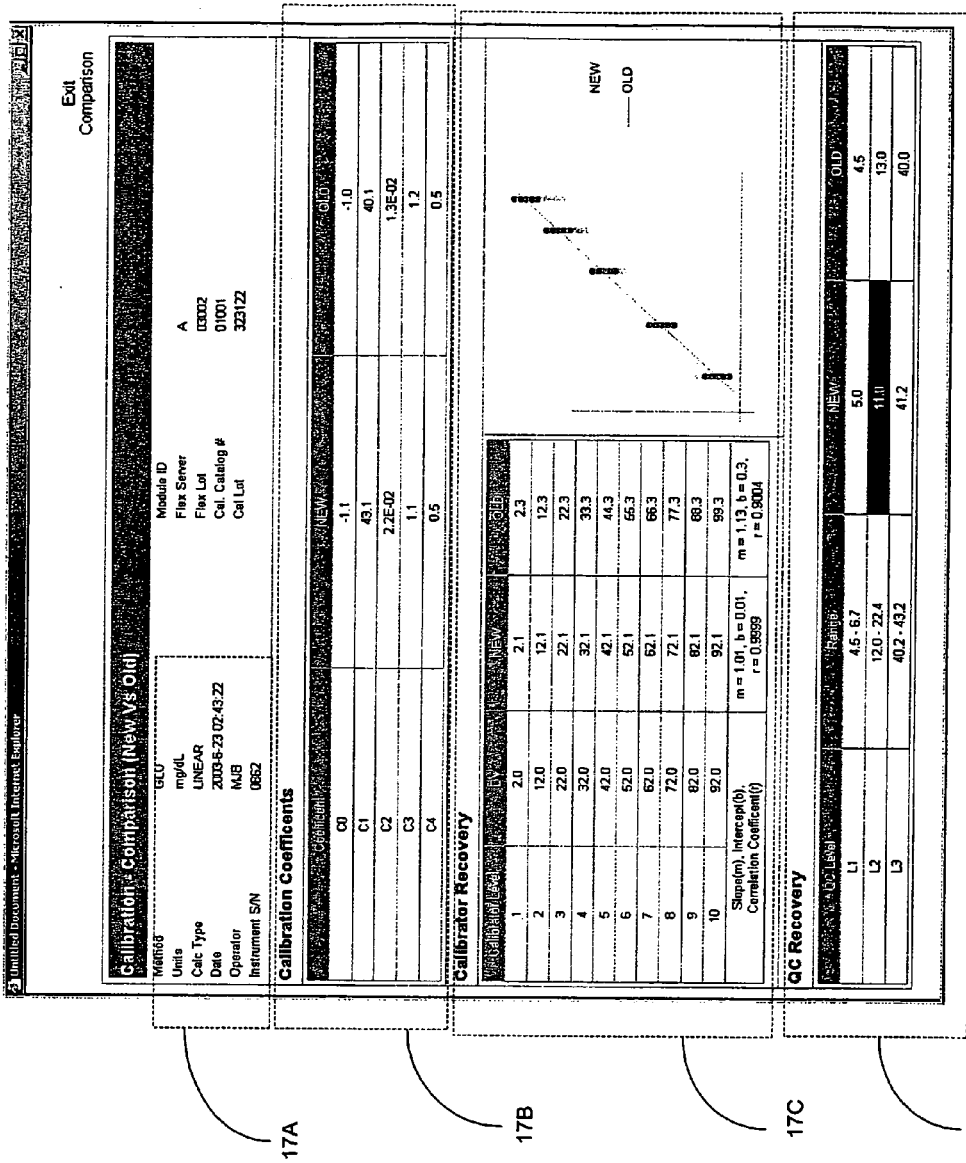

FIG. 17 is an example of a screen having densely detailed and advanced information about details of a current calibration process as compared to the previously used calibration process, including information about the date a particular method was newly calibrated by which operator by which type of calibration as seen in area 17A. The actual values of the calibration curve coefficients may be found in area 17B for the new and the older calibration and in area 17C, actual values for calibration recovery for the new and the older calibration. Area 17D has actual values for calibration recovery for the new and the older calibration. This type of advanced information would rarely and infrequently be accessed, except in unusual circumstances.

FIG. 18 is an example of a screen having densely detailed and advanced information about details of the calibration acceptance criteria analyzer 10 is using to accept or reject analytical results. FIG. 18 includes information about the date the acceptance criteria were activated by which operator for which type of calibration as seen in area 18A. The actual acceptance criteria may be found in area 18B and in area 18C, details of individual acceptance criteria. Again, this type of advanced information would be accessed only by highly qualified personnel for special reasons as it deal with the assay reliability of analyzer 10.

Figure 19:
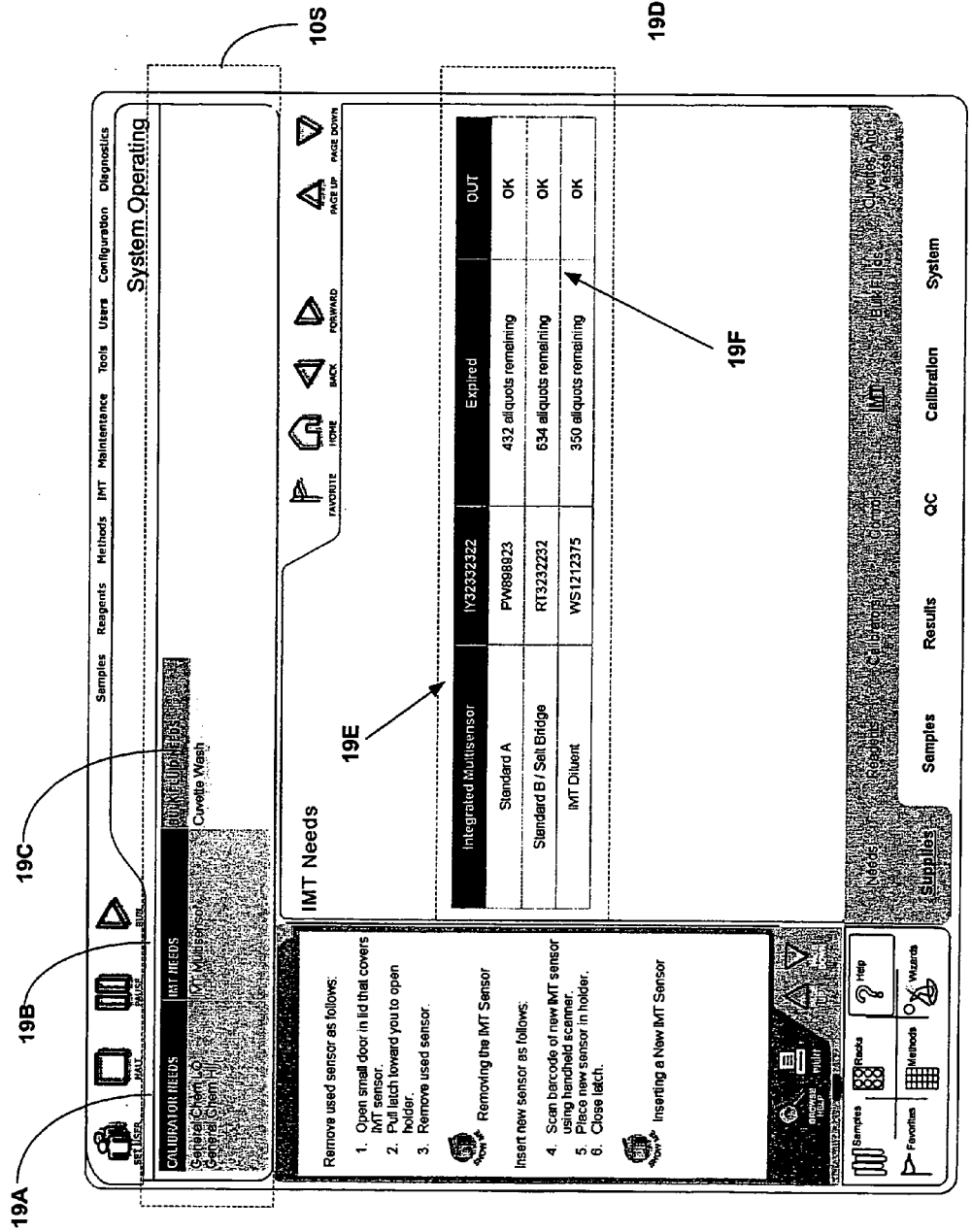
FIG. 19 illustrates an Instrument Status Summary exemplary of the present invention.
Figure 19A:
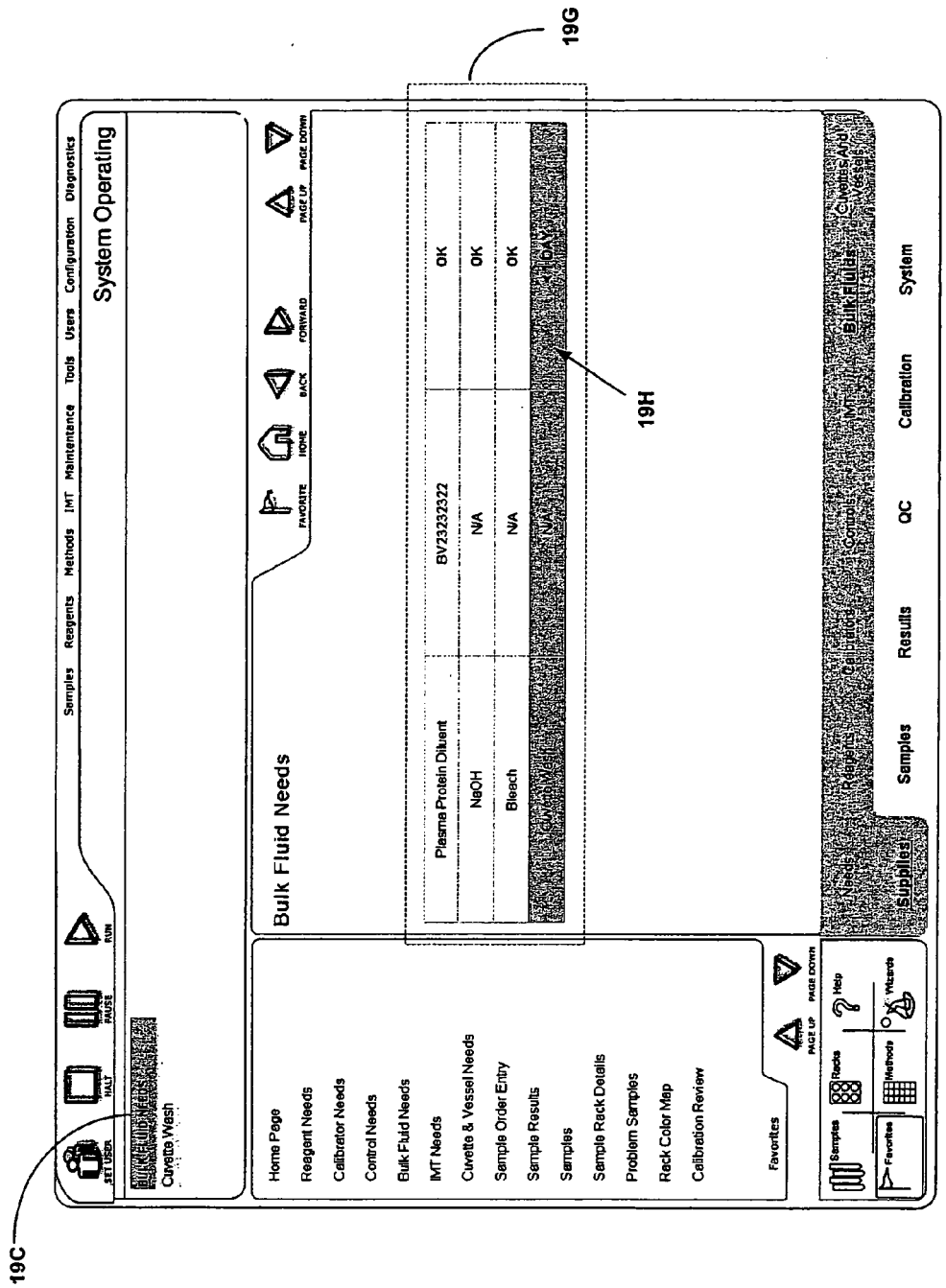
FIG. 19A illustrates an Instrument Status Message exemplary of the present invention.
Figure 19B:
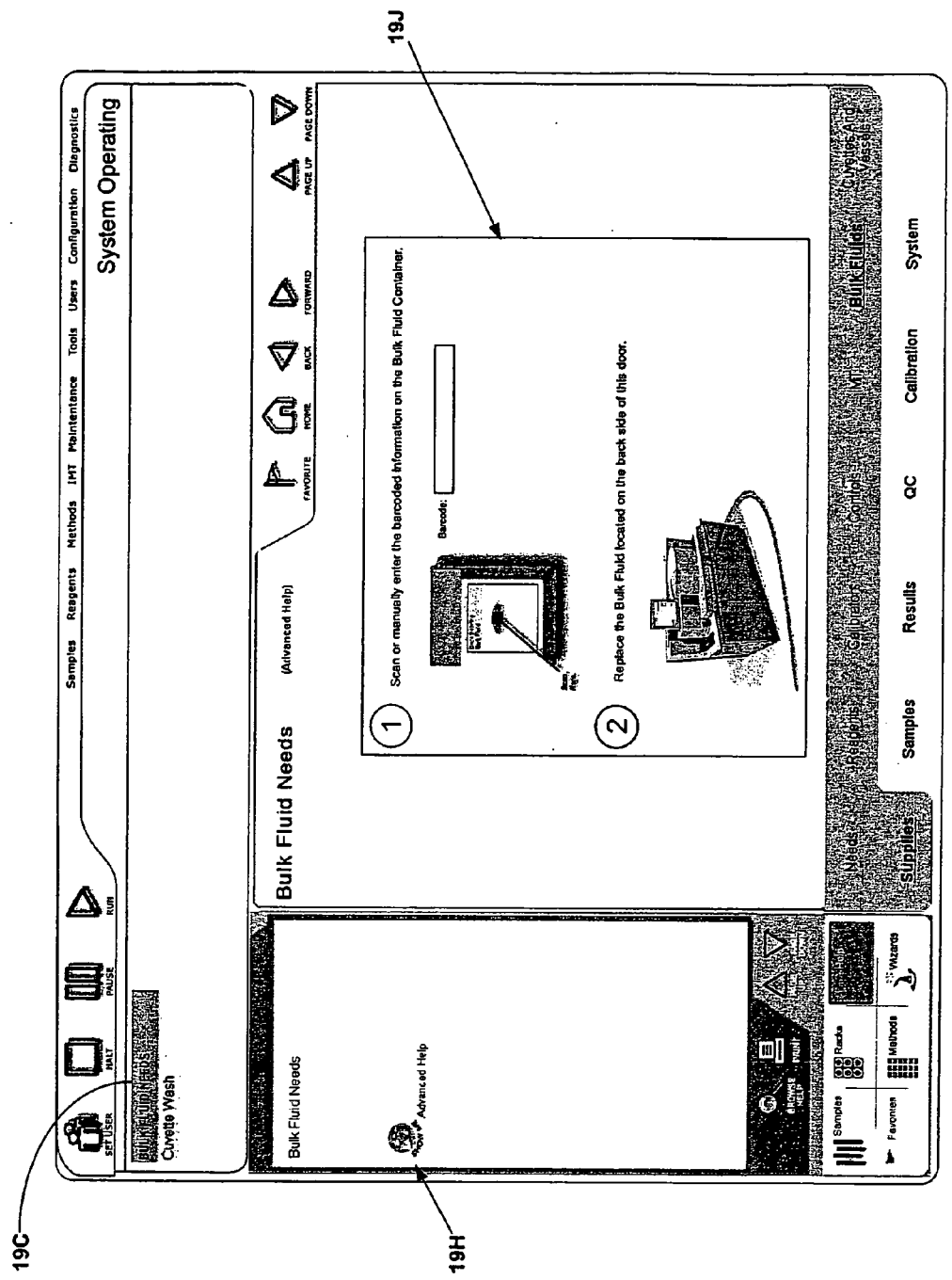
FIG. 19B illustrates an illustration of instrument maintenance message exemplary of the present invention.
Figure 20:
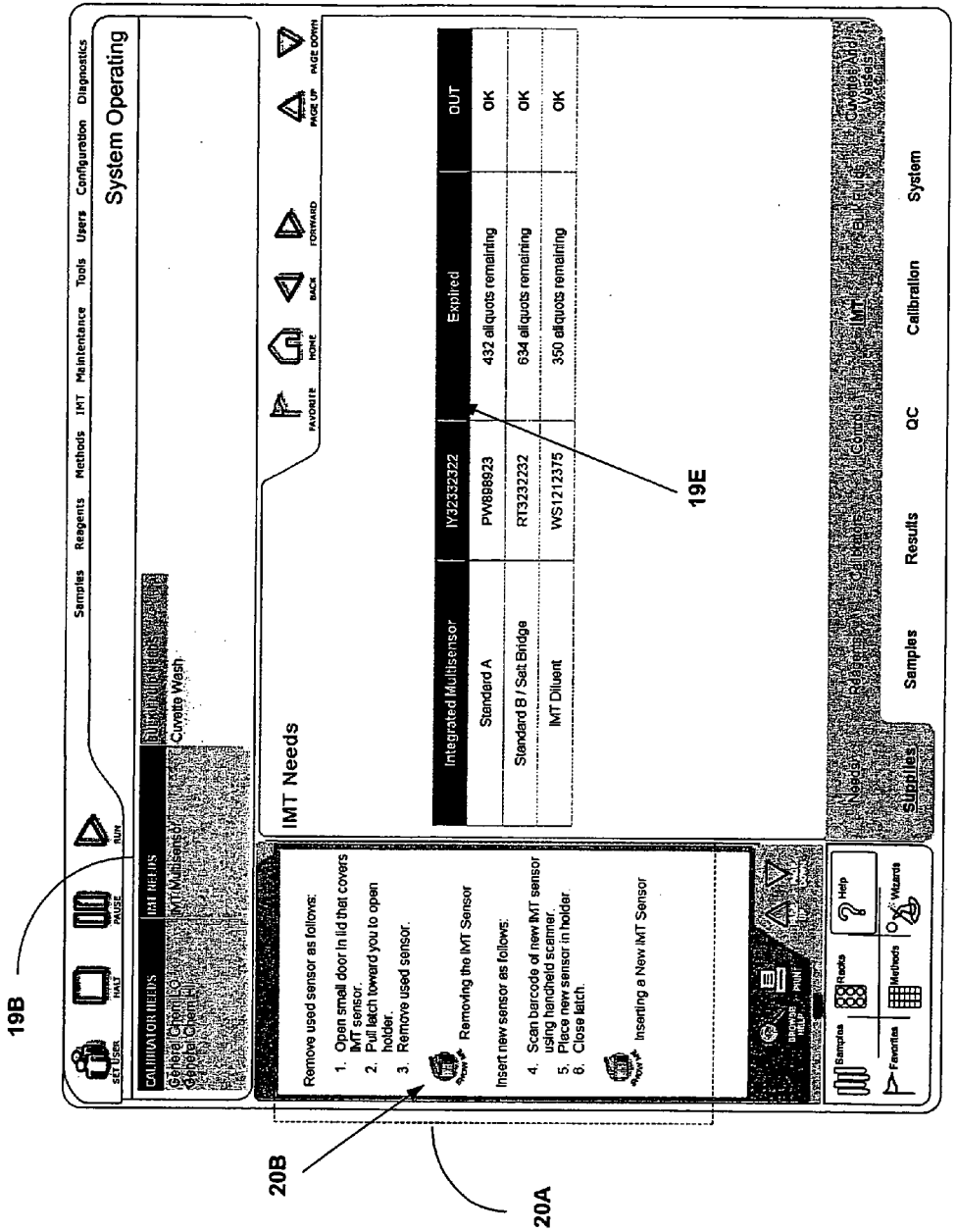
FIG. 20 illustrates trouble-solving information accessible from the screen of FIG. 19.

FIG. 19 illustrates another important feature of the present invention in which Instrument Status Summary tab 10S seen in FIG. 9 comprises a "safe" tab area, like a green colored tab area. If all operational systems within analyzer 10 are functioning within normal ranges, the entire Instrument Status Summary tab will be displayed in the "safe color", green for convenience. If any system within analyzer 10 begins to function outside normal range, "alarm" tab areas like 19A and 19B will appear in a special color, like in a red colored tab, within Instrument Status Summary tab 10S, indicating to an operator that analyzer 10 is not in a fully functional mode of operation. When an operator observes an "alarm" tab areas like 19A and 19B, and simply touches, for example, "alarm" tab area 19B wherein an indication is provided that it is the ion selective electron measuring station 47 which is non-functional, computer 15 is programmed to cause a trouble-shooting tab like 19D to appear, having a highlighted in color or otherwise non-functional identified message 19E identifying exactly what portion of the measuring station 47 is non-functional, optionally also including a message identifying exactly what portions of the measuring station 47 remain functional in message 19F. If the operator then touches non-functional identified message 19E, a trouble-solving tab 20A like seen in FIG. 20 will appear, explaining to the operator what steps to take to correct the problem and restore measuring station 47 to a fully functional state. If the operator is un-certain how to follow the corrective action in trouble-solving tab 20A, he may touch a "Show Me" button 20B, and a series of cartoons 21A or the like will, appear illustrating what steps to take in what order in what portion of analyzer 10. In a similar manner, If any system within analyzer 10 is beginning to approach a state that would cause analyzer 10 to function outside normal range, a "caution" tab areas like 19C will appear in a special color, like in a yellow colored tab, within Instrument Status Summary tab 10S, indicating to an operator that unless certain preventative steps are taken, analyzer 10 will move to an non-functional mode of operation in the near future. When an operator observes an "caution" tab area like 19C, and simply touches "caution" tab area 19C wherein an indication is provided that cuvette wash station 67 needs to be re-supplied with bulk fluids, computer 15 is programmed to cause a preventive-action tab like 19G to appear in FIG. 19A, having a highlighted in color or otherwise identified message 19H identifying exactly what actions need to be taken and completed by when so as to maintain analyzer 10 in a functional state. If the operator is un-certain how to follow the corrective action in preventive-action tab 19G, he may touch a "Show Me" button 19H, and a series of cartoons like cartoon 19J or the like will appear, like seen in FIG. 19B illustrating what steps to take in what order in what portion of analyzer 10.

Another key feature of screen 15S is an operator's ability to define a personalized set of "Favorite Screens" like seen in FIG. 23. Consider that an operator frequently views a screen like Sample Results and wants to eliminate steps to access such information. By simply touching a button 23A marked "Favorites", a hyperlink to the like Sample Results is created to immediately display such a screen and the name of that favorite screen is displayed by name 23C in a Favorites area 23B.

It will be appreciated by those skilled in that art that a number of variations may be made in the above described method and still achieve the essence of the present invention. For these reasons, the present invention is not limited to those embodiments precisely shown and described in the specification but only by the claims.

I claim:

1. A method for displaying information related to the operation of an automated clinical analyzer by:
   providing a visual user interface device with a viewing screen that is adapted to display information pertaining to the control and operating status of the analyzer;
   segmenting the viewing screen so that routine operational information used in routine operation of the analyzer is displayed in a first segment of the viewing screen; and,
   segmenting the viewing screen so that non-routine operational information that is used in a detailed examination of the operation of analyzer is displayed in a second segment of the viewing screen,
   wherein the first segment of the viewing screen comprises at least 90% of the viewing screen, and wherein the non-routine operational information is displayed within dense component based independent windows.

2. The method of claim 1, wherein the second segment of the viewing screen comprises at least 10% of the viewing screen.

3. The method of claim 1, wherein the routine operational information comprises information about entering a sample order, the status of a sample being analyzed, sample results, reagent containers and calibration/Quality Control vial containers needed to be loaded into the analyzer on the next day.

4. The method of claim 1, wherein the non-routine operational information comprises densely detailed and advanced information about which reagent container lot is being used to currently perform each of the different assays analyzer is equipped to perform, expiration dates of each of the reagent lots, calibration status of each of the reagent lots, a relative comparison of calibration coefficients between a new and a previous calibration, and what are the existing calibration acceptance criteria.

5. The method of claim 1 further comprising:
   providing an analyzer status summary tab displayed in a first color if all operational systems within the analyzer are functioning within normal ranges;
   changing the color of the analyzer status summary tab to a second color if any system or component within analyzer is beginning to approach a state that would cause analyzer to function outside a normal operating range; and,
   changing the color of the analyzer status summary tab to a third color range if any system or component within analyzer begins to function outside a normal operating range.

6. The method of claim 5 further comprising touch activating the analyzer status summary tab when in the third color, the touching thereby causing a trouble-solving tab to appear with directions to restore the non-functioning system or component to a fully functional state.

7. The method of claim 6 further comprising touch activating a Show-Me button, the touching thereby causing a series of cartoons to appear illustrating the steps to take and in what order in what portion of the analyzer to restore the non-functioning system or component to a fully functional state.

8. The method of claim 5 further comprising touch activating the analyzer status summary tab when in the second color, the touching thereby causing a trouble-solving tab to appear with directions identifying exactly what actions need to be taken and completed by when so as to maintain analyzer in a functional state.

9. The method of claim 8 further comprising touch activating a Show-Me button, the touching thereby causing a series of cartoons to appear illustrating the steps to take and in what order in what portion of the analyzer to restore the non-functioning system or component to a fully functional state.

* * * * *